US012773311B2

(12) United States Patent
Limem et al.

(10) Patent No.: US 12,773,311 B2
(45) Date of Patent: Oct. 27, 2026

(54) MINIMALLY INVASIVE BREAST SUSPENSION SYSTEM

(71) Applicant: Tepha, Inc., Lexington, MA (US)

(72) Inventors: Skander Limem, Lynnfield, MA (US); Simon F. Williams, Cambridge, MA (US)

(73) Assignee: Tepha, Inc., Lexington, MA (US)

( * ) Notice: Subject to any disclaimer, the term of this patent is extended or adjusted under 35 U.S.C. 154(b) by 497 days.

(21) Appl. No.: 18/273,857

(22) PCT Filed: Jan. 25, 2022

(86) PCT No.: PCT/US2022/013634
§ 371 (c)(1),
(2) Date: Jul. 24, 2023

(87) PCT Pub. No.: WO2022/164779
PCT Pub. Date: Aug. 4, 2022

(65) Prior Publication Data

US 2024/0299157 A1 Sep. 12, 2024

Related U.S. Application Data

(60) Provisional application No. 63/141,743, filed on Jan. 26, 2021.

(51) Int. Cl.
*A61F 2/12* (2006.01)
*A61L 27/26* (2006.01)
(Continued)

(52) U.S. Cl.
CPC ................ *A61F 2/12* (2013.01); *A61L 27/26* (2013.01); *A61L 27/56* (2013.01);
(Continued)

(58) Field of Classification Search
CPC ........ A61F 2/12; A61F 2/0045; A61F 2/0063; A61F 2/0059; A61F 2/2478; A61F 2/52; A61F 2/90; A61F 2/0811
See application file for complete search history.

(56) References Cited

U.S. PATENT DOCUMENTS 8,043,309 B2 10/2011 Catanese, III et al.
9,370,412 B2 6/2016 Robertson
(Continued)

FOREIGN PATENT DOCUMENTS

JP 2006517115 A * 7/2006 ......... A61B 17/0469
WO WO-2023118997 A1 * 6/2023 ....... A61B 17/00491

OTHER PUBLICATIONS

International Search Report and Written Opinion mailed Apr. 11, 2022 for International Application No. PCT/US2022/013634.
(Continued)

*Primary Examiner* — Seema Mathew
(74) *Attorney, Agent, or Firm* — Wolf, Greenfield & Sacks, P.C.

(57) ABSTRACT

Mastopexy implants for lifting the breast of a patient create new tissue planes in the breast that provide a more durable lift, and are particularly useful in lifting breasts with a high content of fatty tissue. The implants can be implanted through stab incisions using blunt dissection, and reduce operating time, and provide an improved aesthetic appearance with minimal scar formation. The implants are designed to be transitory, and have sufficient strength retention to allow the new tissue planes to form and support the lifted breast without any significant loss of support during this regenerative period.

21 Claims, 12 Drawing Sheets

(51) Int. Cl.
*A61L 27/56* (2006.01)
*A61F 2/00* (2006.01)

(52) U.S. Cl.
CPC ................. *A61F 2002/0072* (2013.01); *A61F 2220/0008* (2013.01); *A61L 2430/04* (2013.01)

(56) References Cited

U.S. PATENT DOCUMENTS 9,763,770 B2 9/2017 Lee et al.
11,642,206 B1 * 5/2023 Almulhim ............. A61F 2/0063 606/151
2003/0225420 A1 12/2003 Wardle
2009/0171140 A1 * 7/2009 Chu ...................... A61F 2/0045 600/37
2012/0283826 A1 * 11/2012 Moses ................... A61L 31/146 623/8
2013/0281768 A1 * 10/2013 Dolan ................... A61F 2/0045 600/37
2015/0080648 A1 * 3/2015 Flynn .................... A61F 2/0063 219/121.85
2015/0157438 A1 * 6/2015 Adams .................. A61F 2/0045 600/37
2015/0289969 A1 10/2015 Guterman
2016/0051354 A1 2/2016 Patankar et al.
2016/0106412 A1 4/2016 Petros et al.
2017/0000634 A1 * 1/2017 Helmick ................. A61F 2/186
2021/0346007 A1 * 11/2021 Boileau .................. A61B 17/88
2023/0190439 A1 * 6/2023 Nativ ............... A61B 17/00491 606/213

OTHER PUBLICATIONS

International Preliminary Report on Patentability mailed Aug. 10, 2023 for International Application No. PCT/US2022/013634.
PCT/US2022/013634, Apr. 11, 2022, International Search Report and Written Opinion.
PCT/US2022/013634, Aug. 10, 2023, International Preliminary Report on Patentability.

* cited by examiner

SECTION O-O

DETAIL P

MINIMALLY INVASIVE BREAST SUSPENSION SYSTEM

CROSS-REFERENCE TO RELATED APPLICATIONS

This application is a national stage filing under 35 U.S.C. § 371 of International Application No. PCT/US2022/013634, filed Jan. 25, 2022, which claims the benefit of U.S. Provisional Application Ser. No. 63/141,743, filed Jan. 26, 2021. The contents of these applications are incorporated herein by reference in their entirety.

FIELD OF THE INVENTION

The present invention generally relates to implants and systems that can be used to lift tissues and organs in a minimally invasive manner, and in particular implants and systems that can be used in plastic surgery procedures, including mastopexy. The implants and systems can be used to minimize the formation of scars during lifting procedures, and in particular in the upper pole of the breast.

BACKGROUND OF THE INVENTION

Numerous plastic surgery procedures are performed each year to restore or correct the form or function of the body. Many of these procedures seek to restore a youthful appearance, or even to enhance one's existing appearance. Natural factors, such as aging and gravity, contribute to the loss of youthful appearance. For example, skin laxity, loss of muscle tone, and attenuation of ligaments can result in ptosis (drooping) of the breast. Plastic surgeons have developed a plethora of surgical techniques to correct the ptosis of different anatomical structures that occurs with aging. These techniques vary in the type of incision, direction of incision, plane of dissection, amount of dissection, extent of repositioning of tissue, the use of different types of sutures, different suturing techniques, and different fixation techniques.

Plastic surgeons have developed a number of different mastopexy procedures for lifting the breast. These procedures can, however, be very invasive, require extensive dissection, and can leave the patient with visible scars. For example, the lollipop or vertical mastopexy procedure is performed by making incisions around the areolar, and a vertical incision in the lower pole of the breast from the areolar to the inframammary fold (IMF). The anchor or Wise procedure is an even more invasive procedure than the lollipop procedure where an incision is made across the inframammary fold in addition to the vertical incision used in the lollipop procedure. Both the lollipop and anchor procedures can leave permanent scars on the lower pole of the patient's breast, and in that respect can provide poor cosmetic outcomes.

Less invasive suture-based mastopexy procedures have been developed which help to minimize scar formation. These include the Benelli mastopexy where a donut shaped piece of breast skin is excised from around the areola with an inner incision line following the perimeter of the areola and an outer incision line circling the areola further out. While this approach does minimize scar formation, it can result in serious stretching of the areola or tissue necrosis because all the newly lifted parenchymal weight of the breast is supported by suture surrounding the areola that is used to approximate the breast skin back to the circumference of the areola.

Several surgeons have attempted to reinforce their lift procedures using surgical meshes in open surgery mastopexy and breast reconstruction procedures. Some of these techniques have also incorporated the use of various reinforcing materials similar to those used in hernia repair, such as flat polymeric meshes, allografts, xenografts and autografts. However, wrapping materials around the parenchyma without the use of an anchoring element that shifts the load from the skin of the lower pole can leave the breast subject to the same ptotic forces that were present before breast surgery.

In 1981. Johnson described the use of MARLEX® (polypropylene) mesh to convert the support of breast tissue after mastopexy from a cutaneous origin to a skeletal origin by attaching the mesh to the area of the second rib, (Johnson, *Aesth. Plast. Surg.* 5:77-84 (1981)). The flat MARLEX mesh is a permanent mesh made from polypropylene, and was implanted to provide two slings in each breast that supported the breast tissue. The procedure is based on the Wise open surgery breast lift.

Auclair and Mitz have described a mesh assisted mastopexy using a flat absorbable mesh and a periareolar skin resection technique (Auclair and Mitz, *Ann. Chir. Plast. Esthét.* 38:107-113 (1993)). A rapidly absorbing VICRYL® mesh was placed around the anterior surface of the breast gland in order to form an internal bra. The procedure requires open surgery of the breast, and involves extensive dissection.

Góes has reported the use of polyglactin 910 (an absorbable copolymer of 90% glycolide and 10% L-lactide, also known as VICRYL) and a mixed mesh (containing 60% polyglactine 910 and 40% permanent polyester) in a periareolar mammoplasty using a double skin technique (Góes, *Plast. Reconstr. Surg.* 97:959-968 (1996)). The open surgery technique involves dissecting the soft tissue envelope away from the parenchyma, and wrapping the breast parenchyma with a mesh to help provoke the formation of a vigorous connective scar to produce a breast lining structure that would be less susceptible to ptosis.

U.S. Pat. No. 6,210,439 to Firmin et al. discloses a circular VICRYL mesh with a V-shaped opening extending from its center that has a metallic reinforcing wire running around the periphery. The implant is designed for insertion in an invasive open surgery procedure and assumes a conical shape suitable for mammoplasty when the reinforcing wire is tightened.

U.S. Pat. No. 7,476,249 to Frank discloses an implantable sling shaped prosthesis device for supporting and positioning a breast implant in a patient, wherein the device is configured from a sheet of a chemically inert permanent material, such as polytetrafluoroethylene or silicone, to support the breast implant. The sling shaped device is designed for placement in an open surgery invasive procedure.

US Patent Application Publication No. 2009/0082864 by Chen et al. also discloses a prosthetic device for supporting a breast implant made from a mesh. The device has a flat back wall, a concave front wall, and a curved transitional region between these walls that forms a smoothly curved bottom periphery. Insertion of the device requires an open surgery procedure with significant dissection.

US Patent Application No. 2008/0097601 by Codori-Hurff et al. discloses mastopexy and breast reconstruction procedures assisted by the use of processed tissue material derived from intestine or dermis. The tissue material is cut to a crescent shape to form an implant for mastopexy, and is implanted using an invasive open surgery procedure.

U.S. Patent Application No. 20160038269 to Altman discloses various silk fabric implants that can be implanted using open surgery to support the lower breast.

U.S. Patent Application No. 20120185041 to Mortarino et al. discloses knitted silk meshes that can be used to provide support to the lower pole of the breast.

U.S. Patent Application No. 20130304098 to Mortarino discloses silk implants in the form of pockets that can be used in breast reconstruction.

WO 2009/001293 to Lauryssen discloses polypropylene and polyester mesh implants formed into cup shapes that can be used in mastopexy procedures. The meshes are implanted in open surgery procedures, and completely surround the breast tissue.

WO 2004/096098 to Hamilton discloses a permanent implant formed in a breast shape for soft tissue support, made from polytetrafluoroethylene (ePTFE), which can be used in forming a predetermined breast shape.

WO 2006/117622 to Lauryssen et al. discloses a permanent implant for soft tissue support of the breast that is generally L-shaped or U-shaped, and is wrapped around the breast to provide support.

Van Deventer et al. (*Aesth. Plast. Surg.* 36:578-89 (2012)) have disclosed the use of an internal breast support system for mastopexy using a partially degradable mesh that was formed into a cone (van Deventer et al. *Aesth. Plast. Surg.* 36:578-89 (2012)). The mesh is implanted in an open surgery procedure, and completely surrounds the upper and lower poles of the breast.

U.S. Pat. No. 9,532,867 to Felix discloses absorbable implants for breast surgery that conform to the breast parenchyma. The implants can support newly lifted breast parenchyma.

US 20100023029 to Young discloses a sheet made from VICRYL for use in breast reconstruction with a number of attachment regions for attaching the sheet to the patient's anatomy. The device may be used to partially cover and constrain a tissue expander or implant.

WO2007004214 to Popov discloses a basket-shaped device for supporting the lower pole of a breast. The device is designed to be implanted using open surgery.

Several devices for performing open surgery mastopexy procedures by mimicking the breast's own fascial support system, the circum-mammary ligament, have been described.

US Patent Application No. 2017/0224471 to Rehnke discloses a circular tubular member with a purse string that can be used when the circum-mammary ligament has been stretched or weakened to lift the breast. The device is inserted in an open surgery procedure to tighten the circum-mammary ligament. The device is placed behind the breast gland on top of the pectoral muscle, anchored to the circum-mammary ligament, and cinched to a smaller diameter using the purse string. Cinching causes the base footprint of the breast to narrow, and gathers the breast together in a higher or more projecting position on the patient's chest.

US Patent Application No. 2017/0231753 to Lee discloses a material that is placed on the pectoral muscle below the breast using open surgery to provide circumferential coverage of the breast tissue, stretching and securing the material above the breast, and attaching the material to the chest musculature medial and lateral to the breast in order to elevate the breast tissue.

Several devices for performing mastopexy procedures in a minimally invasive manner using slings have been described.

US Patent Application No. 2008/0027273 by Gutterman discloses a minimally invasive mastopexy system having a soft tissue support sling. The device is designed to provide support by suspending the breast from the upper pole region using a sling.

US Patent Application No. 2012/0283826 by Moses et al. discloses minimally invasive mastopexy systems having an insertion device, a suspension strut, and a lower pole support. The lower pole support is inserted beneath the lower pole of the breast as a sling to lift the breast.

U.S. Patent Application No. 20100217388 to Cohen discloses cradling members for soft tissue shaping of the breast. The cradling member acts as a sling and is implanted to lift the lower pole of the breast.

U.S. Pat. No. 7,670,372 to Shfaram et al. discloses a minimally invasive breast lifting system. The system incorporates one or more suspending members and a cradling member that is placed under the lower pole of the breast. The cradling member is connected to the suspending members, and acts as a sling to lift the breast.

US Patent Application Publication No. 2010/0331612 by Lashinski et al., US 2008/0082113 to Bishop et al., and US 2009/0248071 to Saint et al. discloses a device for performing a minimally invasive mastopexy comprising a sling and soft tissue anchors that are introduced in a superior position to support the breast. US 2012/0053689 to Martin et al. discloses PHA fiber for use in these devices.

SUMMARY OF THE INVENTION

Implants and systems described herein assist the surgeon in reshaping, repositioning or lifting the breast to provide an aesthetically pleasing shape.

In some aspects, implants are provided. In some embodiments, a breast implant may include a unitary elongate member, with a first end and a second end, sized to circumnavigate the breast beneath the skin.

In some aspects, mastopexy systems are provided. In some embodiments, a mastopexy system includes an implantable unitary elongate member, with a first and a second end, sized to circumnavigate the breast beneath the skin, and a sheath connected to the elongate member and at least partially enclosing the member.

In some aspects, methods are provided. In some embodiments, a method of lifting or cinching a breast includes providing one or more introducer tools and a breast implant using the one or more introducer tools to insert the breast implant in a breast so that the breast implant circumnavigates the upper and lower poles of the breast beneath the skin, removing the one or more introducer tools from the breast, and using the breast implant to lift or cinch the breast.

In some aspects, methods are provided. In some embodiments, a method of lifting or cinching a breast includes providing one or more introducer tools and a breast implant including an assembly of an implantable unitary elongate member, with a first and a second end, sized to circumnavigate the upper and lower poles of the breast beneath the skin, and one or more sheaths connected to the member near one or more ends of the member and at least partially enclosing the member. The method also includes using the one or more tools to insert the assembly in the breast so that the member circumnavigates the upper and lower poles of the breast beneath the skin, removing the one or more introducer tools from the breast, removing the one or more sheaths from the breast, and using the member to lift or cinch the breast.

In some aspects, methods are provided. In some embodiments, a method of lifting or cinching a breast includes any combination of the steps described herein.

In some aspects, kits are provided. In some embodiments, a kit for lifting or cinching a breast includes an elongate member, a sheath, and an introducer tool as described herein.

In some aspects, kits are provided. In some embodiments, a kit for lifting or cinching a breast includes any combination of the components described herein.

These advantages as well as other objects and advantages of the present invention will become apparent from the detailed description to follow, together with the accompanying drawings.

BRIEF DESCRIPTION OF THE DRAWINGS

FIG. 2A shows the outline of a patient's breast 10 and a NAC 11, insertion of a first introducer tool 12 of the mastopexy system 13 through a first incision 14. The arrow 15 shows the direction the first introducer tool is advanced in the breast to circumnavigate one side of the breast beneath the skin of the breast. FIG. 2B shows the outline of a patient's breast 20 and a NAC 21, the position of first introducer tool 22 of the mastopexy system 23 after insertion in the breast, and the location of a second incision 24 where the detachable barrel tip 25 of the first introducer tool exits the breast by moving the introducer tool in the direction shown by arrow 26. FIG. 2C shows the outline of a patient's breast 30 and a NAC 31, the position of the detachable barrel tip 32 of the first introducer tool explanted through a second incision 33 in the breast, the position 34 of the assembly of the elongate member covered by the sheath after removal of the first introducer tool (shown in FIG. 2B) with the assembly circumnavigating the breast beneath the skin of the breast from the first incision to the second incision, and the second introducer tool 35 loaded with the remainder of the elongate member ready for insertion on the other side of the patient's breast. FIG. 2D shows the outline of a patient's breast 40 and a NAC 41, the position of the second introducer tool 42 circumnavigating the breast beneath the skin of the breast after insertion through the first incision 43, and the detachable barrel tip 44 of the second introducer tool aimed to exit the breast through the second incision 45 by moving the introducer tool in the direction indicated by arrow 46. FIG. 2E shows the outline of a patient's breast 50 and a NAC 51, with the elongate member 52 circumnavigating the breast beneath the skin of the breast, and the ends 53 of the elongate member exposed from the breast through the second incision 54. Arrows 55 pointing in a superior direction indicate the direction for pulling on the ends 53 of the elongate member to lift the breast.

FIG. 4 shows the structure of the fused ends 73 of the assembly of the elongate member 71 and sheath 72. Detail T shows the cross-sectional structure of sheath 72. Detail U shows enlarged pores 74 of the elongate member. The fused ends 73 of the elongate member and sheaths are shown with perforations 75.

FIG. 7B shows a longitudinal cross-sectional view of the tubular section 121, tubular section's lumen 122, and a detachable barrel tip 123 of the introducer tool. Detail R shown in FIG. 7C shows a longitudinal cross-sectional view of a detachable barrel tip 124 fastened to the first end 125 of the tubular section of an introducer tool 126 by a fastening mechanism. The fastening mechanism is shown with mounting pins 127 located on the detachable barrel tip that are sized for insertion into the first end 125 of the tubular section of the introducer tool 126, and a disengagement notch 128 to release the detachable barrel tip 124 from the first end 125 of the tubular section of the introducer tool 126 by releasing the mounting pins 127. The detachable barrel tip 124 is also shown with a lumen 129 for insertion of the attachment feature (not shown) of the assembly of the elongate member and sheath (not shown). Detail R also shows a latch 130 with two lock pins 131 inserted in the latch receptacle 132 of the detachable barrel tip 124. The detachable barrel tip 124 is shown with a blunt dissection tip 133.

FIG. 8B shows the tubular section 142 of the introducer tool, a detachable barrel tip 143 connected to the first end 144 of the tubular section 142, a slit 145 in the tubular section 142 of the introducer tool, and a cross-section of the tubular section 146 enclosing the assembly 147 of the elongate member and sheath folded into a C-shape.

DETAILED DESCRIPTION OF THE INVENTION

Figure 1:
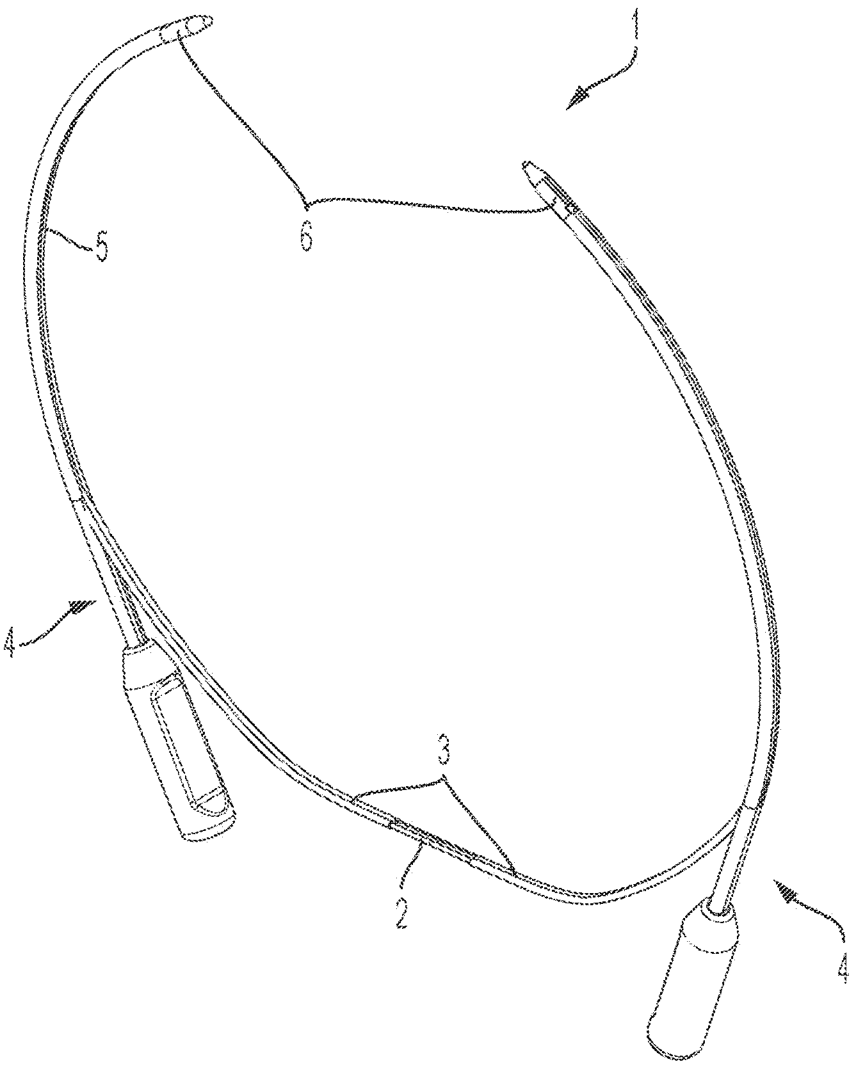
FIG. 1 shows a mastopexy system 1 for minimally invasive breast lift with an assembly of an elongate member 2 partly covered by a sheath 3, and two introducer tools 4, with the introducer tools loaded with the opposite ends of the assembly of the sheath covered elongate member.

The inventors have appreciated that, despite the advances described above, most mastopexy procedures require open surgical procedures with long surgical incisions that leave noticeable and permanent scars on the breast, particularly in the immediate period following the procedure. These scars can leave patients feeling dissatisfied with the aesthetic outcome of the procedure, and disappointed that the procedure failed to meet their expectations. Additionally, the procedures described generally involve extensive dissection of a tissue plane in the lower pole of the breast, and the insertion of a sling or other construct to lift or shape the lower pole. The extensive dissection in these existing procedures usually necessitates the use of general anesthesia, and long recovery times.

In some embodiments, implants and systems for mastopexy may be used to provide a defined aesthetically pleasing outcome without open surgery, large incisions, and extensive dissection and manipulation of tissues, and that minimize the formation of permanent scars on the breast particularly on the upper pole of the breast. It would be particularly desirable to provide implants and systems for mastopexy that can be used to avoid the use of scarring surgical incisions, dissection of tissue planes, the removal of excess skin, and the use of sutures to close incisions. It would be particularly desirable to provide mastopexy implants that can be implanted through small stab incisions. Such procedures could reduce operating time, and the need for general anesthesia. The latter would not only eliminate potential risks associated with general anesthesia and long recovery times related to open surgical procedures, but would provide a more attractive and simpler mastopexy procedure, particularly for some younger patients that may prefer to delay more invasive procedures such as those described above. It would also be desirable to provide implants and systems for minimally invasive mastopexy that can be used in patients with fatty breasts, or less dense breast tissues, where lifting breast tissue is more challenging due to the higher content of fatty tissues present in such breasts.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely." "only" and the like in connection with the recitation of claim elements, or use of a "negative" limitation.

In embodiments, the implants and systems for mastopexy are designed to minimize the formation of scars, reduce operating time, and decrease patient recovery time. The implants may be implanted in the breast of a patient using blunt dissection, through one or more small openings. The implants and systems for mastopexy avoid the use of traditional surgical approaches like the crescent mastopexy, donut (or Benelli) mastopexy, lollipop (or vertical) mastopexy, and the anchor (or Weiss or Wise) mastopexy, which all require extensive surgical incisions normally in conjunction with the removal of patient tissue for inserting mastopexy implants in the breast. In embodiments, the implants are implanted through a single opening in the lower pole of the breast or through a single opening in the upper pole of the breast. In embodiments, the implants for mastopexy are implanted by forming one opening in the lower pole of the breast and one opening in the upper pole of the breast.

In embodiments, the implants and systems for mastopexy comprise unitary elongate members with a first end and a second end, sized to circumnavigate the breast beneath the skin of the breast. In embodiments, the elongate members are sized to circumnavigate the upper and lower poles of the breast beneath the skin of the breast. After implantation in the breast, a force may be applied to the elongate member to lift or cinch the breast. In embodiments, the ends of the elongate member are secured after lifting the breast by affixing the ends of the elongate member to tissue. In embodiments, the ends of the elongate member are secured after lifting the breast by tying together the ends of the elongate member or connecting the ends of the elongate member together.

In embodiments, the implants and systems for mastopexy are designed for use with minimal surgical intervention. In embodiments, the implants are implanted in the breast using stab incisions and blunt dissection. In embodiments, the implants are designed for implantation without the use of general anesthesia.

The length and surface area of the implant's elongate member allows the load of the lifted tissue to be distributed and not localized. Distribution of the load by the elongate member helps to maintain the breast lift and prevent subsequent ptosis. The elongate member is particularly useful in lifting the breasts of patients when the breasts comprise fatty breast tissue, or less dense breast tissue, and when suture cannot be held securely in the fatty breast tissue.

Notably, the elongate member of the implant is not a sling with support lines that are anchored to tissue on the medial and lateral sides of the breast. Instead, the elongate member is designed to circumnavigate the breast beneath the skin of the breast and lift the breast. The elongate member may be secured in the breast by either anchoring the ends of the elongate member in tissue, or by tying the ends of the elongate member together to cinch the breast.

The implants are designed to encourage tissue in-growth. In embodiments, the elongate members of the implants are porous. In embodiments, the elongate members comprise a textile or fabric. In embodiments, the elongate member of the implant comprises a mesh, knitted mesh, crocheted mesh, woven mesh, nonwoven mesh, tape, braid, and film or porous film. In embodiments, the elongate member of the implant comprises a de-tanged mesh. In embodiments, the elongate member of the implant comprises monofilament. In embodiments, the elongate member of the implant comprises oriented monofilament. In embodiments, the oriented monofilament of the elongate member is resorbable. In embodiments, the elongate member comprises fibers with an average diameter between 0.02 mm and 0.7 mm, between 0.05 mm and 0.25 mm, between 0.07 mm and 0.175 mm, and/or any other suitable range of diameters.

In embodiments, the elongate member of the implant is resorbable. In embodiments, the elongate member comprises one or more resorbable polymers. In embodiments, the elongate member retains strength in vivo long enough to allow the support of the breast to be transitioned from the elongate member to new tissue without any loss of support for the lifted breast tissue. In embodiments, the elongate member retains at least 15% of its initial strength, at least 30% of its initial strength, and/or at least 50% of its initial strength after implantation in the breast for 12 weeks. In embodiments, the elongate members function as transitory scaffolds that lift or cinch the breast and provide initial support to the breast, but degrade over time, and are replaced with host tissue.

In embodiments, the elongate member of the implant can withstand a load of at least 5 N, at least 10 N or at least 60 N. In embodiments, the elongate member of the implant can withstand a load of less than 500 N.

In embodiments, the elongate member of the implant can withstand a burst force of at least 1 N, or at least 10 N. In embodiments, the elongate member can withstand a burst force of less than 1,000 N.

In embodiments, the elongate member of the implant may have one or more of the following properties: (i) a suture pullout strength of at least 1 kgf, (ii) a burst strength of 0.1 to 100 kg. 1 to 50 kg. 5-100 kg, 10 to 50 kg, and/or any other suitable burst strength, (iii) a thickness of 0.05 mm. (iv) an areal density of 5 to 800 $g/m^2$, 10 to 1000 $g/m^2$, 20 to 500 $g/m^2$, 5 to 1000 $g/m^2$, 10 to 100 $g/m^2$, 200 to 800 $g/m^2$, and/or any other suitable areal density and (v) a pore diameter of 5 μm to 10 mm, 10 μm to 1 mm, 100 μm to 10 mm, 10 μm to 100 μm, and/or any other suitable pore diameter. In some embodiments, the elongate member of the implant may have one or more of the following properties: (i) a suture pullout strength of 1 kgf to 20 kgf, (ii) a burst strength of 1 to 50 kg or 10 to 50 kg. (iii) a thickness of 0.1 to 1 mm, 0.5 to 2 mm, 0.1 to 0.5 mm, and/or any other suitable thickness, (iv) an areal density of 100 to 300 $g/m^2$, and (v) a pore diameter of 100 μm to 1 mm.

In some embodiments, the elongate member of the implant may have burst strengths between 0.6 and 90 $N/cm^2$, and/or between 1.2 and 30 $N/cm^2$. In embodiments, the elongate member of the implant may have one or more of the following properties: (i) burst strengths between 0.1 to 100 kg, 1 to 50 kg, 5-100 kg, 10 to 50 kg, and/or any other suitable burst strength, (ii) a suture pullout strength of at least 1 kgf, (iii) a burst strength of 0.1 to 100 kg. (iv) a thickness of 0.05-5 mm, 0.1 to 1 mm, 0.1 to 0.5 mm, and/or any other suitable thickness, (v) an areal density of 5 to 800 $g/m^2$, 10 to 1000 $g/m^2$, 20 to 500 $g/m^2$, 5 to 1000 $g/m^2$, 10 to 100 $g/m^2$, 200 to 800 $g/m^2$, and/or any other suitable areal density, and (vi) a pore diameter of 5 μm to 10 mm, 10 μm to 1 mm, 100 μm to 10 mm, 10 μm to 100 μm, and/or any other suitable pore diameter.

In embodiments, the elongate member of the implant comprises a fabric, mesh or textile, and the fabric, mesh or textile may have one or more of the following properties: (i) a suture pullout strength of at least 1 kgf, (ii) a burst strength of 0.1 to 100 kg. 1 to 50 kg, 5-100 kg. 10 to 50 kg, and/or any other suitable burst strength (iii) a thickness of 0.05 mm, (iv) an areal density of 5 to 800 $g/m^2$, 10 to 1000 $g/m^2$, 20 to 500 $g/m^2$, 5 to 1000 $g/m^2$, 10 to 100 $g/m^2$, 200 to 800 $g/m^2$, and/or any other suitable areal density and (v) a pore diameter of 5 μm to 10 mm, 10 μm to 1 mm, 100 μm to 10 mm, 10 μm to 100 μm, and/or any other suitable pore diameter. In some embodiments, the elongate member of the implant includes a fabric, mesh or textile, and the fabric, mesh or textile may have one or more of the following properties: (i) a suture pullout strength of 1 kgf to 20 kgf, (ii) a burst strength of 1 to 50 kg or 10 to 50 kg. (iii) a thickness of 0.1 to 1 mm, 0.5 to 2 mm, 0.1 to 0.5 mm, and/or any other suitable thickness, (iv) an areal density of 100 to 300 g/m$^2$, and (v) a pore diameter of 100 μm to 1 mm.

In embodiments, the elongate member of the implant comprises poly-4-hydroxybutyrate (P4HB) or copolymers thereof. In embodiments, the elongate member of the implant comprises poly(butylene succinate) (PBS) or copolymer thereof. In embodiments, the elongate member of the implant comprises polydioxanone. In embodiments, the elongate members of the implants comprise P4HB or copolymers thereof, PBS or copolymers thereof, or polydioxanone in the form of a fabric, textile or mesh, a monofilament fabric, mesh or textile made from a monofilament, and/or made from an oriented monofilament. In embodiments, the elongate member comprises one or more polymers, wherein the one or more polymers are synthesized from, or comprise, one or more of the following monomers: glycolic acid, lactic acid, 1,4-dioxanone, trimethylene carbonate, 3-hydroxybutyric acid, 4-hydroxybutyric acid, ε-caprolactone, 1,4-butanediol, adipic acid and succinic acid.

In embodiments, the systems for mastopexy comprise the unitary elongate member of the implant, with a first end and a second end, sized to circumnavigate the breast beneath the skin of the breast, and a sheath connected to the member and at least partially enclosing the member. In embodiments, the elongate member of the implant is sized to circumnavigate the upper and lower poles of the breast beneath the skin of the breast. In embodiments, an end of the sheath is connected to an end of the elongate member to form an assembly of the elongate member and sheath. In embodiments, an end of a sheath is fused to an end of the elongate member to form an assembly. In embodiments, the assembly of the sheath fused to the elongate member further comprises an attachment feature to connect the assembly of the implant comprising the elongate member and sheath to an introducer tool. In embodiments, the attachment feature comprises one or more holes perforated in the region where the elongate member is fused to the sheath. In embodiments, the attachment feature of the assembly of the elongate member and sheath is connected to an introducer tool. In embodiments, the introducer tool comprises a tubular section, with a first end and a second end, with the first end of the tubular section connected to a detachable barrel tip, the second end of the tubular section connected to a handle, and the tubular section comprising a slit running at least part of its length. In embodiments, the slit in the tubular section is sized to receive at least part of the assembly of the elongate member and sheath. In embodiments, the cross-section of at least part of the tubular section of the introducer tool has a C-shape with a cavity sized to allow insertion of the implant comprising the elongate member inside the tubular section of the introducer. In embodiments, at least part of the cross-section of the assembly of the implant comprising the elongate member and sheath is formed into a C-shape or folded so that it fits inside at least part of the tubular section of the introducer. In embodiments, the introducer tool further comprises a detachable barrel tip with a latch receptacle to secure the attachment feature of the assembly of the elongate member and sheath to the detachable barrel tip. In embodiments, the system for mastopexy further comprises a latch, and the latch can be used to secure the attachment feature of the implant's elongate member and sheath to the latch receptacle of the detachable barrel tip. In embodiments, the latch comprises one or more lock pins that can be inserted through one or more holes in the attachment feature. In embodiments, the introducer tool comprises a fastening mechanism that allows the detachable barrel tip to be attached or detached from the first end of the tubular section of the introducer tool. In embodiments, the fastening mechanism comprises one or more mounting pins for attachment of the detachable barrel tip to the first end of the tubular section of the introducer tool, and a disengagement notch for releasing the detachable barrel tip from the first end of the tubular section of the introducer tool. In embodiments, the detachable barrel tip comprises a terminal blunt dissection tip or cutting tip. In embodiments, the tubular section of the introducer tool further comprises an inlet opening. In embodiments, the inlet opening is located near the second end of the tubular section of the introducer tool. In embodiments, the mastopexy system is constructed by inserting the assembly of the implant comprising the elongate member and sheath at least partly in the tubular section of the introducer tool, optionally through an inlet opening in the tubular section of the introducer tool. In embodiments, the mastopexy system is constructed by: (i) inserting the fused section of the assembly through an inlet opening positioned near the second end of the tubular section of the introducer tool, (ii) advancing the fused section inside the tubular section towards the first end of the tubular section of the introducer tool until it exits the first section of the tubular section of the introducer tool, (iii) inserting the fused section of the assembly in the latch receptacle of the detachable barrel tip which is attached to the first end of the tubular section of the introducer tool, and (iv) inserting the lock pins of the latch through the attachment feature of the assembly, and securing the latch in the latch receptacle to anchor the fused section to the detachable barrel tip.

In embodiments, the mastopexy system comprises an implant comprising an elongate member comprising one or two fastening anchors. The fastening anchors are designed to anchor the elongate member in place after the breast has been lifted. In embodiments, the fastening anchors may comprise a hole sized to receive a suture. A suture can be passed through the hole, and used to anchor the fastening anchor to tissue in order to secure the elongate member in place. The fastening anchors are located near one end or both ends of the elongate member, about 2-10 cm from the ends of the elongate members. In embodiments, the fastening anchors have a T-shape. In embodiments, the fastening anchors are formed with a T-cap pin containing a hole sized to receive a suture, and two arms that connect the T-cap pin to the elongate member.

In embodiments, the mastopexy system comprises two identical introducers and one elongate member of the implant wherein the elongate member is at least partly enclosed by one or more sheaths, and the elongate member comprises fused sections of the elongate member and sheath at each end that can be anchored to detachable barrel tips at the first ends of each introducer.

In embodiments, the elongate member of the implant is a fabric, tape, ribbon, film, porous film, textile, knitted mesh, woven mesh or de-tanged mesh. In embodiments, the elongate member comprises one or more polymers. In embodiments, the one or more polymers comprise one or more monomers selected from the group: glycolic acid, lactic acid, 1,4-dioxanone, trimethylene carbonate, 3-hydroxybutyric acid, 4-hydroxybutyric acid, ε-caprolactone, 1,4-butanediol, adipic acid, and succinic acid.

In embodiments, a method of lifting a breast is provided comprising the steps of: (i) inserting one or more introducer tools and an implant comprising an elongate member sized to circumnavigate the upper and lower poles of the breast in the breast so that the elongate member circumnavigates the upper and lower poles of the breast beneath the skin of the breast, (ii) removing the one or more introducer tools from the breast, and (iii) using the elongate member to lift or cinch the breast. In embodiments, the method of lifting the breast further comprises at least partly covering the elongate member with one or more sheaths to form an assembly prior to insertion of the elongate member in the breast, inserting the assembly of the elongate member and one or more sheaths in the breast using one or more introducer tools, removing the one or more introducer tools from the breast, and removing the one or more sheaths from the breast before lifting or cinching the breast with the elongate member. In embodiments, the method of lifting further comprises forming an attachment feature at one or both ends of the elongate member at least partly covered by a sheath, attaching an introducer tool to an attachment feature, and using the introducer tool to insert the elongate member in the breast. In embodiments, the method of lifting further comprises providing an introducer tool with a tubular section and slit running at least part of its length, connecting the attachment feature of the assembly to a detachable barrel tip located at the end of the introducer tool, and inserting at least partly the assembly of the elongate member and sheath into the tubular section of the introducer tool. In embodiments, the method of lifting further comprises providing the detachable barrel tip with a dissection tip or cutting tip, and using the tip to form a channel that circumnavigates the upper and lower poles of the breast beneath the skin of the breast. In embodiments, the method of lifting further comprises implanting the implant comprising the elongate member in the channel that circumnavigates the upper and lower poles of the breast. In embodiments, the method of lifting further comprises providing the detachable barrel tip with a fastening mechanism for attachment and detachment of the detachable barrel tip from the introducer tool, using the fastening mechanism to connect the attachment feature of the elongate member to the detachable barrel tip, inserting the introducer tool with the elongate member in the breast, and using the fastening mechanism to detach the detachable barrel tip from the introducer tool and removing the detachable barrel tip from the breast. In embodiments, the method of lifting further comprises removing the detachable barrel tip connected to the attachment feature from the breast, and then withdrawing the introducer tool minus the detachable barrel tip from the breast. In embodiments, the method of lifting comprises removing the detachable barrel tip through a small opening in the upper pole of the breast, and removing the remainder of the introducer tool through a small opening in the lower pole of the breast. In embodiments, the method of lifting comprises removing the detachable barrel tip through a small opening in the lower pole of the breast, and removing the remainder of the introducer tool through a small opening in the upper pole of the breast. In embodiments, the method of lifting further comprises providing a detachable barrel tip with a latch receptacle and latch, and inserting the latch through the attachment feature and into the latch receptacle to secure the elongate member to the introducer tool.

In embodiments, a method of lifting the breast comprises the steps of: (i) providing an implant comprising an elongate member with a first end and second end, (ii) introducing the first end of the elongate member in the lower pole of the breast or at the IMF, circumnavigating the lower and upper pole of the breast beneath the skin of the breast on the lateral side of the breast with the elongate member, (iii) explanting the first end of the elongate member from the upper pole of the breast, (iv) introducing the second end of the elongate member in the lower pole of the breast or at the IMF at the same location where the first end of the elongate member was introduced, circumnavigating the lower and upper pole of the breast beneath the skin of the breast on the medial side of the breast with the elongate member, (v) explanting the second end of the elongate member at the same location where the first end of the elongate member was explanted from the upper pole of the breast, (vi) pulling the first and second ends of the elongate member to lift the breast, and (vii) securing the ends of the elongate member to maintain the lift of the breast.

In embodiments, a method of lifting the breast comprises the steps of: (i) providing an implant comprising an elongate member with a first end and second end, (ii) introducing the first end of the elongate member in the upper pole of the breast, circumnavigating the upper and lower poles of the breast beneath the skin of the breast on the lateral side of the breast with the elongate member, (iii) explanting the first end of the elongate member from the lower pole of the breast or the IMF, (iv) introducing the second end of the elongate member in the upper pole of the breast at the same location where the first end of the elongate member was introduced, circumnavigating the upper and lower poles of the breast beneath the skin of the breast on the medial side of the breast with the elongate member, (v) explanting the second end of the elongate member at the same location where the first end of the elongate member was explanted from the lower pole of the breast or the IMF. (vi) pulling the first and second ends of the elongate member to lift the breast, and (vii) securing the ends of the elongate member to maintain the lift of the breast.

In embodiments, a method of lifting the breast comprises the steps of: (i) providing an implant including an elongate member with a first end and second end, (ii) introducing the first end of the elongate member in the breast in the lower pole of the breast, or at the IMF, circumnavigating the lower and upper poles of the breast beneath the skin of the breast with the elongate member, (iii) explanting the first end of the elongate member from the breast at the position where the first end of the elongate member was introduced into the breast or at the IMF, (iv) pulling the first and second ends of the elongate member to lift the breast, and (v) securing the ends of the elongate member to maintain the lift of the breast. In embodiments, the methods of lifting further comprises (a) introducing the first end of the elongate member using an introducer tool with a detachable tip, wherein the detachable tip is connected to an end of the elongate member, (b) explanting the end of the elongate member from the breast by turning the detachable tip of the introducer tool towards the skin of the breast, (c) advancing the introducer tool until the tip is explanted from the breast, (d) detaching the tip connected to the elongate member from the introducer tool, (c) removing the introducer tool from the breast, (f) applying tension to the ends of the elongate member to lift the breast, and (g) optionally trimming the ends of the elongate member, and securing the elongate member to maintain the position of the lifted breast.

In embodiments, the method of lifting the breast comprises implanting the implant comprising the elongate member in the breast, and using the elongate member to lift the breast by making only one incision for implanting and lifting the breast. In embodiments, the method of lifting the breast comprises implanting the elongate member in the breast, and using the elongate member to lift the breast by making a single incision at the IMF or in the lower breast.

In embodiments, the method of lifting the breast comprises: (i) providing one or more introducer tools and an assembly comprising an implantable implant comprising a unitary elongate member, with a first and a second end, sized to circumnavigate the upper and lower poles of the breast beneath the skin of the breast, and one or more sheaths connected to the elongate member near one or more ends of the member and at least partially enclosing the member, (ii) inserting the assembly in the breast using the one or more introducer tools so the elongate member circumnavigates the upper and lower poles of the breast beneath the skin of the breast, (iii) removing the one or more introducer tools from the breast, (iv) removing the one or more sheaths from the breast, and (v) lifting or cinching the breast with the elongate member. In embodiments, the method of lifting the breast further comprises forming an attachment feature at one or both ends of the elongate member, connecting the attachment feature at one or both ends of the elongate member to one or more introducer tools, and using the one or more introducer tools to insert the elongate member in the breast. In embodiments, the method of lifting the breast further comprises inserting, at least partly, the assembly of the elongate member and sheath into a tubular section of the introducer tool, wherein the tubular section has a slit running at least part of its length with an inlet opening for inserting the assembly, a first end connected to a detachable barrel tip, and a second end connected to a handle. In embodiments, the method of lifting the breast further comprises connecting the attachment feature of the elongate member to the detachable barrel tip. In embodiments, the method of lifting the breast further comprises using the detachable barrel tip of the introducer tool to form a channel that circumnavigates the upper and lower poles of the breast beneath the skin of the breast sized for implantation of the elongate member. In embodiments, the method of lifting the breast further comprises detaching the detachable barrel tip from the introducer tool after insertion of the assembly of the elongate member and sheath in the breast, and withdrawing the introducer tool from the breast.

In embodiments, the method of lifting the breast comprises affixing the elongate member to tissue after lifting or cinching the breast, or tying the ends of the elongate member together after lifting or cinching the breast.

In embodiments, the method of lifting the breast comprises implanting a resorbable elongate member. In embodiments, the resorbable elongate member is formed from one or more polymers, wherein the polymers are synthesized from, or comprise, one or more of the following monomers: glycolic acid, lactic acid, 1,4-dioxanone, trimethylene carbonate, 3-hydroxybutyric acid, 4-hydroxybutyric acid, ε-caprolactone, 1,4-butanediol, adipic acid and succinic acid.

In embodiments, a method of forming a mastopexy system comprises: forming an implant comprising an elongate member by knitting, weaving, braiding, extruding or casting, and inserting the elongate member, at least partly, in a sheath. In embodiments, the elongate member is knitted into a mesh, and the mesh is de-tanged. In embodiments, the method of forming the mastopexy system further comprises forming an assembly of the elongate member and sheath by connecting the sheath and the elongate member together, or fusing the sheath and member together, at an end of the elongate member, to form an attachment feature, and connecting the assembly to an introducer tool using the attachment feature. In embodiments, the method of forming the mastopexy system further comprises connecting the elongate member and sheath together, or fusing the sheath and member together, at both ends of the elongate member to form two attachment features, and connecting each attachment feature to an introducer tool. In embodiments, the attachment features are formed by fusing the elongate member and sheath together to form an assembly of the elongate member and sheath, and cutting one or more holes where the member and sheath were fused together. In embodiments, the method of forming the mastopexy system further comprises forming one or more introducer tools with a tubular section, with a first end and a second end, and a slit running at least part of the tubular section's length, connecting a detachable barrel tip to the first end of the tubular section, and attaching a handle to the second end of the tubular section. In embodiments, the method of forming the mastopexy system further comprises forming the detachable barrel tip with a terminal blunt dissection tip or cutting tip. In embodiments, the method of forming the mastopexy system further comprises forming a latch receptacle for securing the attachment feature to the detachable barrel tip. In embodiments, the method of forming the mastopexy system further comprises forming the introducer tool with a fastening mechanism to allow attachment and detachment of the detachable barrel tip from the first end of the tubular section. In embodiments, the fastening mechanism is formed using one or more mounting pins to attach the detachable barrel tip to the tubular section of the introducer tool, and a disengagement notch to release the detachable barrel tip from the tubular section of the introducer tool. In embodiments, the method of forming the mastopexy system further comprises securing the attachment feature of the assembly of the elongate member and sheath to the latch receptacle of the detachable barrel tip using a latch, wherein the latch has one or more lock pins. In embodiments, the method of forming the mastopexy system further comprises inserting the assembly of the elongate member and sheath, at least partly, into the tubular section of the introducer tool through the slit in the tubular section.

In embodiments, a method for performing mastopexy comprises forming a loop around the breast beneath the skin with a unitary elongate member, reducing the diameter of the loop to project the breast; and securing ends of the elongate member together subsequent to the step of reducing. In embodiments, the method is performed through two or less stab incisions. In embodiments, the method is performed without affixing the elongate member to bone or ligaments.

In embodiments, the elongate member has a cross section similar to that of a ribbon or tape.

In embodiments, the mastopexy system comprises a tensioner. The tensioner may be used to adjust the tension on the elongate member, and thereby adjust the extent of the breast lift or cinching of the breast.

In embodiments, the elongate members may be implanted without the removal of patient tissues. The elongate members may be implanted without removal of the patient's skin.

In embodiments, the implants comprising the elongate members are implanted using blunt dissection by inserting a blunt dissection tool in the breast, pushing the tool through the breast tissue with a penetration force sufficient to penetrate tissue and form a channel in the breast for the elongate member.

In embodiments, the implant comprising the elongate member serves to provide the surgeon with a means to deliver cells, stem cells, gels, hydrogels, bioactive agents, drugs, biological agents, fatty tissue, autologous fat, fat lipoaspirate, adipose cells, fibroblast cells, and other materials to the implant site.

In embodiments, the implant comprising the elongate member has an endotoxin content of less than 20 endotoxin units. In embodiments, the implantable components of the mastopexy system are sterile. The implantable components may be sterilized with ethylene oxide, cold ethylene oxide, electron beam irradiation, or gamma irradiation.

The implants, mastopexy systems, and methods described herein differ substantially from other implants and methods previously disclosed for mastopexy and breast reconstruction.

First, the implants are designed to be implanted in a minimally invasive manner, and not by open surgical procedures that result in extensive dissection of the breast and significant scarring of the breast. The implants are designed for implantation in the breast using one or two small incisions (e.g., stab incisions). The elongate member of the implant is not placed in the breast by a highly invasive open surgical procedure, and does not lift the breast by pulling on a draw cord. Second, the implants are designed to be anchored at a single location in the breast unlike slings which are anchored at two locations, usually on the lateral and medial sides of the breast, to form a hammock under the lower pole of the breast. In some embodiments, the implants may be designed to be anchored at the IMF, or in the lower breast, anterior to the NAC, or alternatively the implants are designed to be anchored superior to the NAC (as opposed to anchoring on the medial and lateral sides of the breast). Third, the implant comprises a unitary elongate member to lift the breast. The implant is not formed by implanting multiple components in the breast. The elongate member is present in both the upper and lower breast of the patient. Fourth, the implant is sized to lift the breast by circumnavigating the breast beneath the skin of the breast. The implant is not sized to form a sling that cannot circumnavigate the breast. Fifth, the elongate member of the implant is designed to be deployed in vivo at least partly from at least one sheath. Sixth, the mastopexy system is designed with an introducer comprising a detachable barrel tip that is connected to the elongate member of the implant. After implantation of the elongate member in the breast, the detachable barrel tip can be explanted from the breast, and detached from the introducer tool. Seventh, the breast is not suspended using sutures, but rather an elongate member is used to circumnavigate the entire breast beneath the skin of the breast, cinch and lift the breast. Eighth, the elongate member of the implant is implanted by forming a channel that circumnavigates the breast. Ninth, the elongate member has a first and second end. The elongate member does not have a ring or circular structure.

Figure 2B:
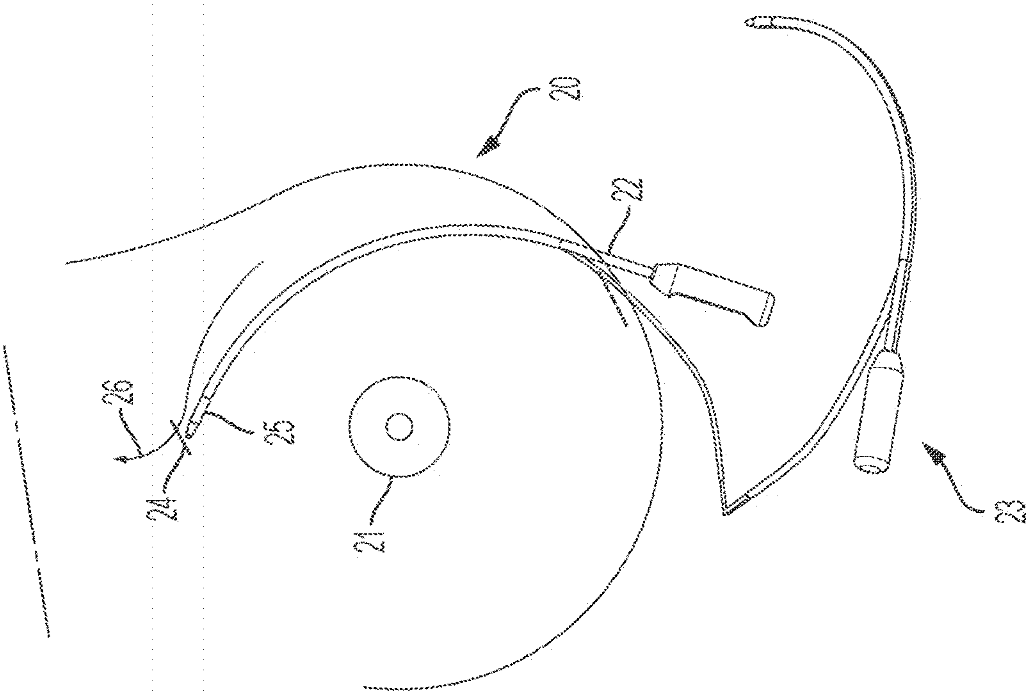
FIGS. 2A-E shows steps to perform a minimally invasive mastopexy lift using the mastopexy system shown in FIG. 1.
Figure 2A:
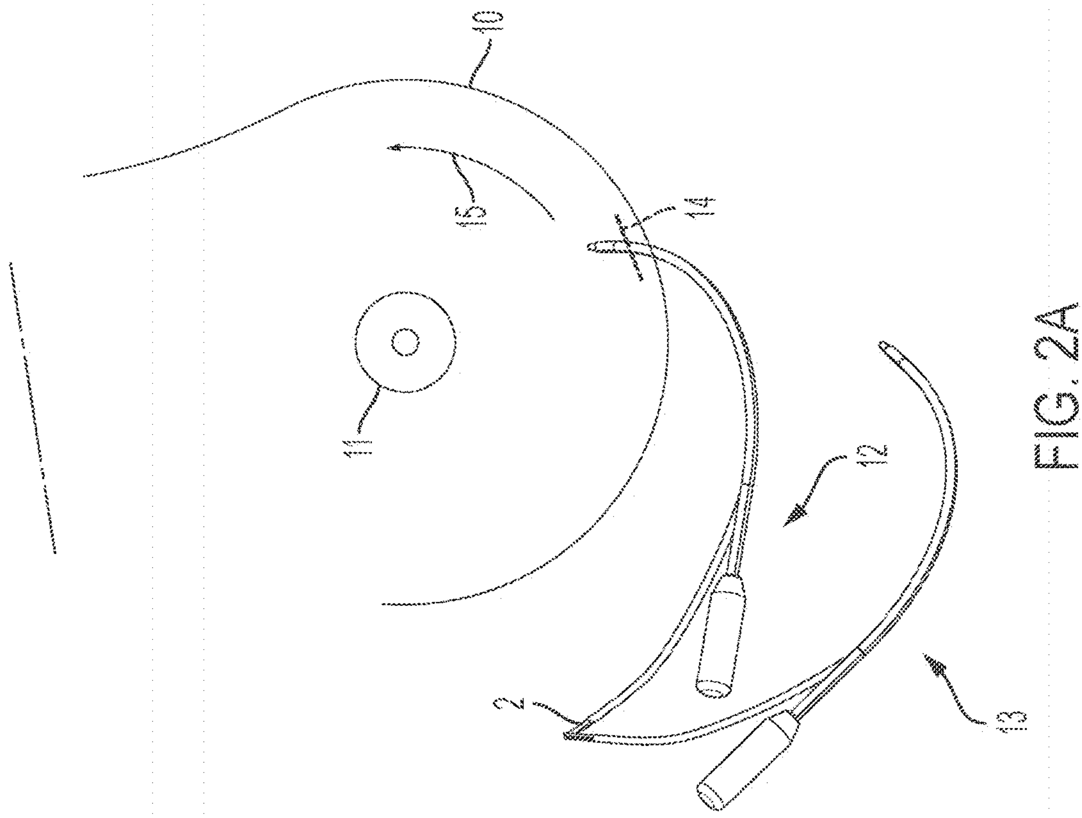

Now turning to FIG. 1 and FIGS. 2A-E, a system for minimally invasive breast lift and a procedure for using the system for breast lift in a patient's breast are depicted for facilitating understanding of the invention. Particularly, FIG. 1 shows a system 1 for minimally invasive breast lift composed of an assembly of an implant comprising an elongate member 2 partly covered by a sheath 3, and two introducer tools 4 loaded with the opposite ends of the assembly of the sheath covered elongate member. The introducer tools comprise tubular sections with slits 5 to allow insertion of the assembly of the sheath covered elongate member inside the tubular sections. The introducer tools 4 are fitted with detachable barrel tips 6 that are connected to the ends of the assembly of the elongate member and sheath. The system 1 is implanted in the breast of a patient to lift or cinch the breast as shown, for example, in FIG. 2A-E. FIG. 2A shows the outline of a patient's breast 10 and a NAC 11, the insertion of a first introducer tool 12 of the system 13 for minimally invasive breast lift in the breast of a patient through a first incision 14. The introducer tool 12 is either inserted in the lower pole of the patient's breast, and/or at the IMF of the patient, and advanced to circumnavigate the breast beneath the skin of the breast in the direction indicated by arrow 15.

FIG. 2B shows the outline of a patient's breast 20 and a NAC 21, with the first introducer tool 22 of the mastopexy system 23 inserted in the breast, and the location of a second incision 24 where the detachable barrel tip 25 of the first introducer tool exits the breast in the upper pole of the breast by moving the introducer tool in the direction shown by arrow 26.

Figure 2D:
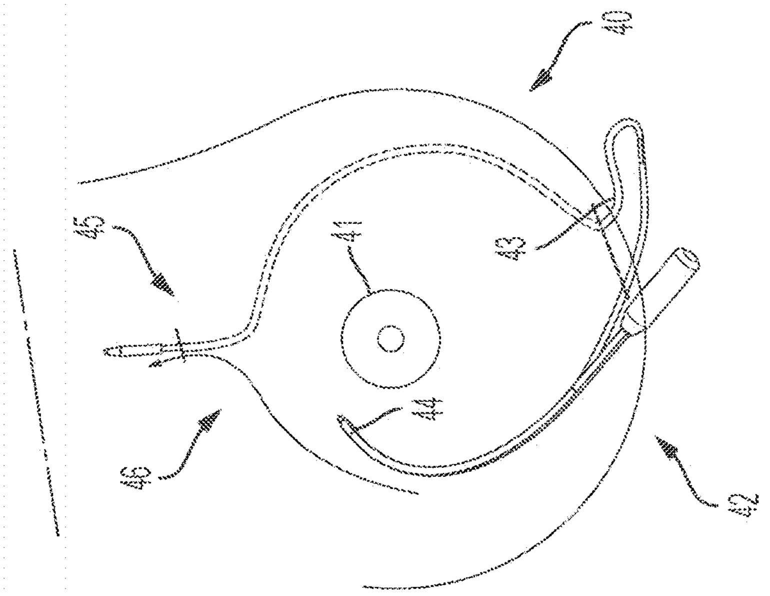
Figure 2C:
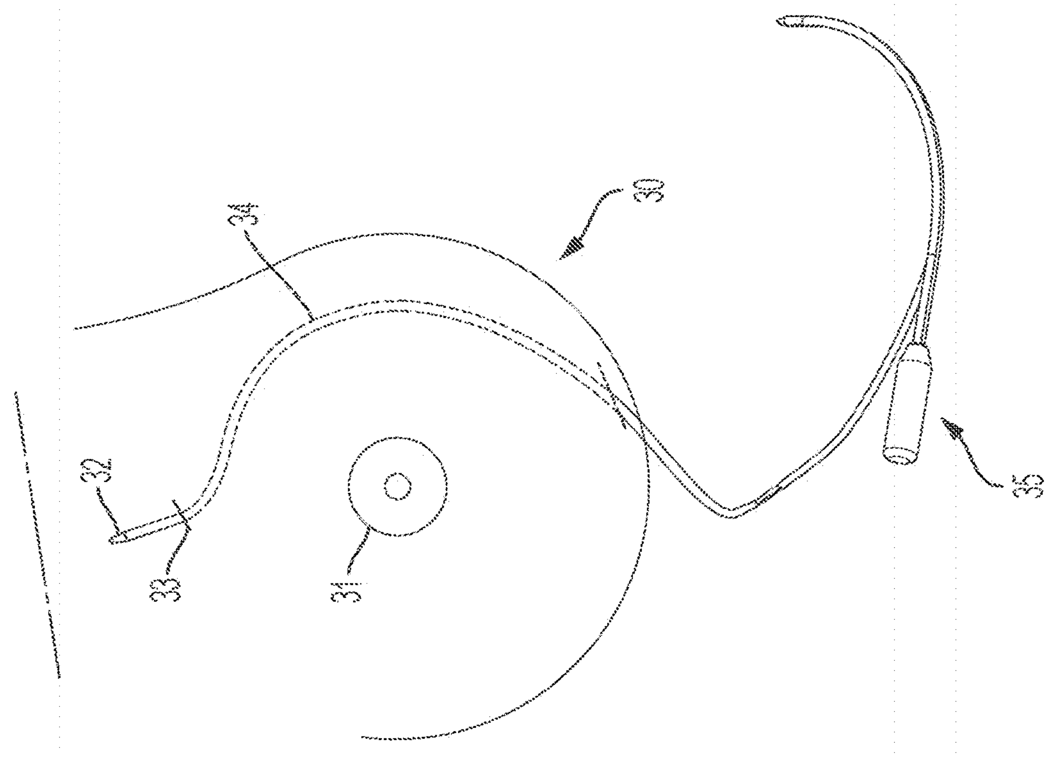

FIG. 2C shows the outline of a patient's breast 30 and a NAC 31 with the detachable barrel tip 32 of the first introducer tool explanted through a second incision 33 in the upper pole of the breast, the position 34 in the breast of the assembly of the elongate member covered by the sheath after removal of the first introducer tool with the assembly circumnavigating the breast beneath the skin of the breast from the first incision to the second incision, and the second introducer tool 35 loaded with the remainder of the elongate member ready for insertion on the other side of the patient's breast.

FIG. 2D shows the outline of a patient's breast 40 and a NAC 41, with a second introducer tool 42 inserted through the first incision 43 and circumnavigating the opposite side of the breast beneath the skin of the breast, with the detachable barrel tip 44 of the second introducer tool aimed to exit the breast through the second incision 45 by moving the introducer tool in the direction indicated by arrow 46.

Figure 2E:
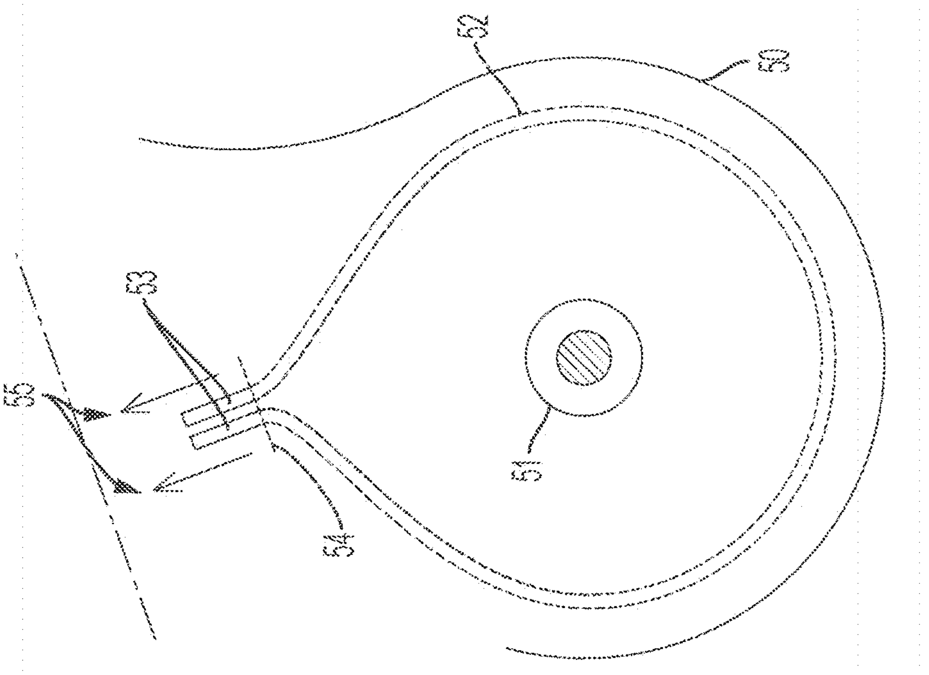

FIG. 2E shows the outline of a patient's breast 50 and a NAC 51, with the elongate member 52 circumnavigating the breast beneath the skin of the breast after the ends 53 of the elongate member have both been explanted at the second incision 54 and after the detachable barrel tips and sheath have been removed from the elongate member. The mastopexy procedure is completed by pulling the ends 53 of the elongate member in a superior direction as indicated by arrows 55, and securing and trimming the elongate member to maintain the breast lift.

To further assist in understanding the following definitions are set forth below. However, it is also to be appreciated that unless defined otherwise as described herein, all technical and scientific terms used herein have the same meaning as commonly understood by one of ordinary skill in the art to which this invention belongs.

Definitions

"Bioactive agent" as generally used herein refers to therapeutic, prophylactic or diagnostic agents, agents that promote healing and the regeneration of host tissue, and also therapeutic agents that prevent, inhibit or eliminate infection. "Bioactive agent" includes a single such agent and is also intended to include a plurality.

"Blend" as generally used herein means a physical combination of different polymers, as opposed to a copolymer formed of two or more different monomers.

"Burst strength" as used herein unless otherwise stated is determined by test method based on ASTM D6797-02 "Standard test method for bursting strength of fabrics constant rate of extension (CRE) ball burst test," using an MTS Q-Test Elite universal testing machine or similar device. However, the testing fixture uses a ⅜ inch diameter ball, and the opening is ½ inch diameter.

"Copolymers of poly-4-hydroxybutyrate" as generally used herein means any polymer containing 4-hydroxybutyrate with one or more different hydroxy acid units.

"Copolymers of poly(butylene succinate)" as generally used herein means any polymer of succinic acid and 1,4-butanediol monomers incorporating one or more additional monomers. Examples of copolymers of poly(butylene succinate) include poly(butylene succinate-co-adipate), poly (butylene succinate-co-terephthalate), poly(butylene succinate-co-ethylene succinate), and poly(butylene succinate-co-propylene succinate). Poly(butylene succinate-co-adipate), for example, may be made by condensation polymerization from succinic acid, adipic acid and 1,4-butanediol. Copolymers of poly(butylene succinate) include polymers comprising (i) succinic acid and 1,4-butanediol units, and (ii) one or more of the following additional units, such as: chain extenders, cross-linking agents, and branching agents. Examples of these agents include malic acid, citric acid, tartaric acid, and glycerol. Examples of copolymers of poly(butylene succinate) include: succinic acid-1,4-butanediol-malic acid copolyester, succinic acid-1,4-butanediol-citric acid copolyester, succinic acid-1,4-butanediol-tartaric acid copolyester, succinic acid-1,4-butanediol-malic acid copolyester further comprising citric acid, tartaric acid, or a combination thereof, succinic acid-adipic acid-1,4-butanediol-malic acid copolyester, succinic acid-adipic acid-1,4-butanediol-citric acid copolyester, succinic acid-adipic acid-1,4-butanediol-tartaric acid copolyester, or succinic acid-adipic acid-1,4-butanediol-malic acid copolyester further comprising citric acid, tartaric acid, or combinations thereof. Copolymers of poly(butylene succinate) also include polymers comprising succinic acid and 1,4-butanediol units and one or more hydroxycarboxylic acid unit or triol unit. The copolymers may also comprise maleic or fumaric acid units, or combinations thereof.

"Diameter" as generally used herein is determined according to the US Pharmacopeia (USP) standard for diameter of surgical sutures (USP 861).

"Endotoxin content" as generally used herein refers to the amount of endotoxin present in an implant or sample, and is determined by the limulus amebocyte lysate (LAL) assay.

"Inframammary fold" or "IMF" as generally used herein is the position where the lower pole of the breast meets the chest wall.

"Lower pole" as generally used herein means the part of the breast located between the inframammary fold (IMF) and the nipple meridian reference, and protruding away from the chest wall.

"Molecular weight" as generally used herein, unless otherwise specified, refers to the weight average molecular weight (Mw), not the number average molecular weight (Mn), and is measured by GPC relative to polystyrene.

"Orientation" as generally used herein refers to the alignment of polymer chains within a material or construct. For example, oriented fibers means that some or all of the polymer chains within a fiber have been aligned.

"PBS" as used herein means poly(butylene succinate).

"Poly-4-hydroxybutyrate" as generally used herein means a homopolymer containing 4-hydroxybutyrate units. It can be referred to herein as P4HB or TephaFLEX® biomaterial (manufactured by Tepha, Inc., Lexington, MA).

"Pore size" as generally used herein is calculated using open source 25 ImageJ software available at https://imagej.nih.gov/ij/index.html.

"Resorbable" as generally used herein means the material is degraded in the body, and the degradation products are eliminated or excreted from the body. The terms "absorbable", "resorbable", "degradable", and "erodible", with or without the prefix "bio", can be used interchangeably herein, to describe materials broken down and gradually absorbed, excreted, or eliminated by the body, whether degradation is due mainly to hydrolysis or mediated by metabolic processes.

"Strength retention" refers to the amount of time that a material maintains a particular mechanical property following implantation into a human or animal. For example, if the tensile strength of a resorbable fiber decreased by half over 3 months when implanted into an animal, the fiber's strength retention at 3 months would be 50%.

"Sub-glandular" as used herein in the context of breast implant placement means the implant is placed beneath the glands of the breast, but superficial to the pectoral muscle.

"Sub-pectoral" as used herein in the context of breast implant placement means the implant is placed beneath the pectoral muscle of the chest.

"Suture pullout strength" as used herein means the peak load (kg) at which an implant fails to retain a suture. It is determined using a tensile testing machine by securing an implant in a horizontal holding plate, threading a suture in a loop through the implant at a distance of 1 cm from the edge of the implant, and securing the suture arms in a fiber grip positioned above the implant. Testing is performed at a crosshead rate of 100 mm/min, and the peak load (kg) is recorded. The suture is selected so that the implant will fail before the suture fails.

"Unitary" as generally used herein means a single unit or continuous entity.

"Upper pole" as generally used herein means the top part of the breast located between the upper pole reference and the nipple meridian reference, and protruding away from the chest wall.

"Yarn" as used herein means a continuous strand of textile fibers, or filaments. The yarn may be twisted, not twisted, or substantially parallel strands.

Materials for Preparing Implants and Systems for Mastopexy

In embodiments, implants and mastopexy systems have been developed using a wide variety of materials to perform a minimally invasive mastopexy procedure. The implants produce an aesthetically pleasing breast by lifting tissue in the breast. The systems and implants avoid the need for extensive dissection of the breast that usually results in scarring of the skin. The use of the implants and mastopexy systems eliminate the need to use sling devices in mastopexy procedures to lift the lower pole of the breast. The mastopexy systems decrease the time required to lift the breast, and decrease patient morbidity. The implanted elongation members may be made of resorbable materials which degrade after implantation leaving no foreign body in the breast. During resorption of the resorbable materials, tissue ingrowth into the elongation members results in new tissue planes that support the breast lift and prevent ptosis.

A. Polymers for Preparing Implants and Systems for Mastopexy

The mastopexy implants may comprise permanent materials, such as non-degradable thermoplastic polymers, including polymers and copolymers of ethylene and propylene, including ultra-high molecular weight polyethylene, ultra-high molecular weight polypropylene, nylon, polyesters such as poly(ethylene terephthalate), poly(tetrafluoroethylene), polyurethanes, poly(ether-urethanes), poly (methyl methacrylate), polyether ether ketone, polyolefins, and poly(ethylene oxide). However, the implants may comprise resorbable materials, thermoplastic or polymeric resorbable materials, and, in some embodiments, the implants may be made substantially from resorbable materials. In embodiments, systems for mastopexy may comprise permanent materials used to facilitate delivery of the implant, and implants comprising resorbable materials. For example, the mastopexy system may comprise an implant comprising an elongate member comprising a resorbable material, a sheath used for delivery of the implant that is made from a permanent material, and one or two introducer tools comprising metal.

In some embodiments, the implants are made from one or more resorbable polymers, and/or resorbable thermoplastic polymers and copolymers. The implant may, for example, be prepared from polymers including, but not limited to, polymers of glycolic acid, lactic acid, 1,4-dioxanone, trimethylene carbonate, 1,4-butanediol, succinic acid, adipic acid, 3-hydroxybutyrate, 4-hydroxybutyrate, ε-caprolactone, including polyglycolic acid, polylactic acid, polydioxanone, polycaprolactone, copolymers of glycolic and lactic acids, such as VICRYL®, MAXON®, and MONOCRYL® polymers, and including poly(lactide-co-caprolactones); poly (orthoesters); polyanhydrides; poly(phosphazenes); polyhydroxyalkanoates (PHA's); synthetically or biologically prepared polyesters; polycarbonates; tyrosine polycarbonates; polyamides (including synthetic and natural polyamides, polypeptides, and poly(amino acids)); polyesteramides; poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); silk (including recombinant silks and silk derivatives and analogs); chitin; chitosan; modified chitosan; keratin, biocompatible polysaccharides; hydrophilic or water soluble polymers, such as polyethylene glycol, (PEG) or polyvinyl pyrrolidone (PVP), with blocks of other biocompatible or biodegradable polymers, for example, poly(lactide), poly(lactide-co-glycolide), or polycaprolactone and copolymers thereof, including random copolymers and block copolymers thereof. In some embodiments, the resorbable polymer or copolymer will be substantially resorbed after implantation within a 1 to 24-month timeframe, and/or a 3 to 18-month timeframe. The resorbable polymer may retain some residual strength for at least 2 weeks to 3 months.

Blends of polymers, such as resorbable polymers, can also be used to prepare the mastopexy implants. Blends of resorbable polymers are prepared from resorbable polymers including, but not limited to, polymers comprising glycolic acid, lactic acid, 1,4-dioxanone, trimethylene carbonate, 1,4-butanediol, succinic acid, adipic acid, 3-hydroxybutyrate, 4-hydroxybutyrate, &-caprolactone or copolymers thereof.

In some embodiments, poly-4-hydroxybutyrate (Tepha's P4HB™ polymer, Lexington, MA) or a copolymer thereof is used to make the implant. Copolymers include P4HB with another hydroxyacid, such as 3-hydroxybutyrate, and P4HB with glycolic acid or lactic acid monomer. Poly-4-hydroxybutyrate is a strong, pliable thermoplastic polyester that is biocompatible and resorbable (Williams, et al. Poly-4-hydroxybutyrate (P4HB): a new generation of resorbable medical devices for tissue repair and regeneration, Biomed. Tech. 58(5):439-452 (2013)). Upon implantation, P4HB hydrolyzes to its monomer, and the monomer is metabolized via the Krebs cycle to carbon dioxide and water. In some embodiments, the P4HB homopolymer and copolymers thereof have a weight average molecular weight, Mw, within the range of 50 kDa to 1,200 kDa (by GPC relative to polystyrene) and/or from 100 kDa to 600 kDa. A weight average molecular weight of the polymer of 50 kDa or higher may enhance processing and mechanical properties.

In another embodiment, the mastopexy implants comprise a polymer comprising at least a diol and a diacid. In some embodiments, the polymer used to prepare the mastopexy implant is poly(butylene succinate) (PBS) wherein the diol is 1,4-butanediol and the diacid is succinic acid. The poly (butylene succinate) polymer may be a copolymer with other diols, other diacids or a combination thereof. For example, the polymer may be a poly(butylene succinate) copolymer that further comprises one or more of the following: 1,3-propanediol, 2,3-butanediol, ethylene glycol, 1,5-pentanediol, glutaric acid, adipic acid, terephthalic acid, malonic acid, methylsuccinic acid, dimethylsuccinic acid, and oxalic acid. Examples of poly(butylene succinate) copolymers are: poly(butylene succinate-co-adipate), poly(butylene succinate-co-terephthalate), poly(butylene succinate-co-butylene methylsuccinate), poly(butylene succinate-co-butylene dimethylsuccinate), poly(butylene succinate-co-ethylene succinate) and poly(butylene succinate-co-propylene succinate). The poly(butylene succinate) polymer or copolymer thereof may also further comprise one or more of the following: chain extender, coupling agent, cross-linking agent and branching agent. For example, the poly (butylene succinate) polymer or copolymer thereof may be branched, chain extended, or cross-linked by adding one or more of the following agents: malic acid, trimethylol propane, trimesic acid, glycerol, citric acid, glycerol propoxylate, and tartaric acid. Agents for branching, chain extension, or crosslinking the poly(butylene succinate) polymer or copolymer thereof are triols, tricarboxylic acids, and hydroxycarboxylic acid units. The hydroxycarboxylic acid unit may have two carboxylic groups and one hydroxyl group, two hydroxyl groups and one carboxyl group, three carboxyl groups and one hydroxyl group, or two hydroxyl groups and two carboxyl groups. In some embodiments, the breast implants may include poly(butylene succinate) comprising malic acid as a branching, chain extending, or cross-linking agent. This poly(butylene succinate) copolymer may be referred to as poly(butylene succinate) cross-linked or chain-extended with malic acid, succinic acid-1, 4-butanediol-malic acid copolyester, or poly(1,4-butylene glycol-co-succinic acid), cross-linked or chain-extended with malic acid. It should be understood that references to malic acid and other cross-linking agents, coupling agents, branching agents and chain extenders include polymers prepared with these agents wherein the agent has undergone further reaction during processing. For example, the agent may undergo dehydration during polymerization. Thus, poly (butylene succinate)-malic acid copolymer refers to a copolymer prepared from succinic acid, 1,4-butanediol and malic acid. In another embodiment, malic acid may be used as a branching, chain-extending or cross-linking agent to prepare a copolymer of poly(butylene succinate) with adipate, which may be referred to as poly[(butylene succinate)-co-adipate] cross-linked or chain-extended with malic acid. As used herein, "poly(butylene succinate) and copolymers" includes polymers and copolymers prepared with one or more of the following: chain extenders, coupling agents, cross-linking agents and branching agents. In some embodiments, the poly(butylene succinate) and copolymers thereof contain at least 70%, 80%, 90%, and/or any other suitable percentage by weight of succinic acid and 1,4-butanediol units. In another embodiment, the breast implants comprise poly (butylene succinate) or copolymer thereof comprising glycerol as a branching, chain extending, or cross-linking agent.

The polymers comprising diacid and diols, including poly(butylene succinate) and copolymers thereof and others described herein, may have a weight average molecular weight (Mw) of 10,000 Da to 400,000 Da, 50,000 Da to 300,000 Da and/or 100,000 Da to 200,000 Da based on gel permeation chromatography (GPC) relative to polystyrene standards. In some embodiments, the polymers and copolymers have a weight average molecular weight of 50,000 Da to 300,000 Da and/or 75,000 Da to 300,000 Da. In some embodiments, the poly(butylene succinate) or copolymer thereof used to make the implant, or a component of the implant, has one or more, or all of the following properties: density of 1.23-1.26 g/cm$^3$, glass transition temperature of −31° C. to −35° C., melting point of 113° C. to 117° C., melt flow rate (MFR) at 190° C./2.16 kgf of 2 to 10 g/10 min, and tensile strength of 30 to 60 MPa.

B. Additives

Certain additives may be incorporated into the implant, for example in the resorbable polymer, copolymer or blends thereof that are used to make the implant. These additives may be incorporated during a compounding process to produce pellets that can be subsequently melt-processed. For example, pellets may be extruded into fibers suitable for making the implants. In another embodiment, the additives may be incorporated using a solution-based process, for example, fibers may be spun from solutions of the polymer and one or more additives.

In some embodiments, the additives may be biocompatible. In some embodiments, the additives may be both biocompatible and resorbable.

In one embodiment, the additives may be nucleating agents and/or plasticizers. These additives may be added in sufficient quantity to produce the desired result. In general, these additives may be added in amounts between 1% and 20% by weight. Nucleating agents may be incorporated to increase the rate of crystallization of the polymer, copolymer or blend. Such agents may be used, for example, to facilitate fabrication of the implant, and to improve the mechanical properties of the implant. Examples of nucleating agents include, but are not limited to, salts of organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine.

Plasticizers that may be incorporated into the compositions for preparing the implants include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydrofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof. Examples of plasticizers are citrate esters.

C. Bioactive Agents

The implants can be loaded or coated with bioactive agents. Bioactive agents may be included in the implants for a variety of reasons. For example, bioactive agents may be included in order to improve tissue in-growth into the implant, to improve tissue maturation, to provide for the delivery of an active agent in vivo, to improve wettability of the implant, to prevent infection, and to improve cell attachment. The bioactive agents may also be incorporated into the structure of the implant.

The implants may contain cellular adhesion factors, including cell adhesion polypeptides. As used herein, the term "cell adhesion polypeptides" refers to compounds having at least two amino acids per molecule that are capable of binding cells via cell surface molecules. The cell adhesion polypeptides include any of the proteins of the extracellular matrix which are known to play a role in cell adhesion, including fibronectin, vitronectin, laminin, elastin, fibrinogen, collagen types I, II, and V, as well as synthetic peptides with similar cell adhesion properties. The cell adhesion polypeptides also include peptides derived from any of the aforementioned proteins, including fragments or sequences containing the binding domains.

The implants may incorporate wetting agents designed to improve the wettability of the surfaces of the implant structures to allow fluids to be easily adsorbed onto the implant surfaces, and to promote cell attachment and or modify the water contact angle of the implant surface. Examples of wetting agents include polymers of ethylene oxide and propylene oxide, such as polyethylene oxide, polypropylene oxide, or copolymers of these, such as PLURONICS®. Other suitable wetting agents include surfactants or emulsifiers.

The implants can contain gels, hydrogels or living hydrogel hybrids. These materials may be used to further improve wetting properties of the implant or to promote cellular growth throughout the thickness of the implant. Hydrogel hybrids consist of living cells encapsulated in a biocompatible hydrogel like gelatin, methacrylated gelatin (GelMa), silk gels, and hyaluronic acid (HA) gels.

The implants may contain active agents designed to stimulate cell in-growth, including growth factors, cellular differentiating factors, cellular recruiting factors, cell receptors, cell-binding factors, cell signaling molecules, such as cytokines, and molecules to promote cell migration, cell division, cell proliferation and extracellular matrix deposition. Such active agents include fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insulin-like growth factor (IGF), hepatocyte growth factor (HGF), interleukin-1-B (IL-1 B), interleukin-8 (IL-8), and nerve growth factor (NGF), and combinations thereof.

Other bioactive agents that can be incorporated in the implants include antimicrobial agents, in particular antibiotics, disinfectants, oncological agents, anti-scarring agents, anti-inflammatory agents, anesthetics, small molecule drugs, anti-angiogenic factors and pro-angiogenic factors, immunomodulatory agents, and blood clotting agents. The bioactive agents may be proteins such as collagen and antibodies, peptides, polysaccharides such as chitosan, alginate, keratin, hyaluronic acid and derivatives thereof, nucleic acid molecules, small molecular weight compounds such as steroids, inorganic materials such as hydroxyapatite, or complex mixtures such as platelet rich plasma. Suitable antimicrobial agents include: bacitracin, biguanide, triclosan, gentamicin, minocycline, rifampin, vancomycin, cephalosporins, copper, zinc, silver, and gold. Nucleic acid molecules may include DNA, RNA, siRNA, miRNA, antisense or aptamers.

The implants may also contain allograft material and xenograft materials, including acellular dermal matrix material and small intestinal submucosa (SIS).

Additionally, human fat such as autologous fat grafts may be added or injected across or into the implant. Lipoaspirate fatty tissue from the patient may be added to the internal surface or external surface of the implant. In areas where the implant is porous, the fatty tissue and globules may be held in place within the pores of the implant.

In another embodiment, the collected fatty tissue is mixed with a natural or synthetic fluidized scaffolding matrix to be added to the implant to assist in holding the globules of fat in place in the implant. Examples of natural and synthetic fluidized scaffolding matrix include, without limitation, hydrogels, water soluble polymers, polyesters, and hydrophilic polymers, including polyethylene oxide, polyvinyl alcohol, and polymers of fibrin, thrombin, alginate, collagen, chitosan, and silk.

In some embodiments, the implants may incorporate systems for the controlled release of the therapeutic or prophylactic agents.

Components for Preparing Mastopexy Implants

A variety of methods can be used to manufacture the implants and systems for mastopexy. The implants may comprise the fibers disclosed herein.

Elongate Members

In embodiments, the implants of the mastopexy systems comprise elongate members. The elongate members can be used to lift the breast of a patient. The elongate members are not slings that are designed to make a hammock underneath the lower pole of the breast, and the elongate members are not anchored to the chest wall either side of the breast in order to lift the breast. Instead, the elongate members are implanted to circumnavigate the breast beneath the skin of the breast, and the breast is lifted by tightening the elongate member. The breast may be cinched by tightening the elongate member circumnavigating the breast. Tightening the elongate member circumnavigating the breast decreases the diameter of the elongate member circumnavigating the breast. As the elongate member is tightened, the breast is gathered together in a higher position. As the elongate member is tightened, the breast is positioned in a more projecting position on the chest. In embodiments, the elongate member is resorbable, and constitutes an internal resorbable bra that lifts and stabilizes the breast. In embodiments, the elongate members are transitory scaffolds. That is, the elongate members are designed to lift the breast, and then be replaced by new tissue as the elongate member degrades. Over time, the support of the breast provided by the elongate member is replaced by support from host tissue. In this manner, the breast is lifted by the elongate member, but maintained longer-term in its lifted position by in-grown breast tissue. In embodiments, the elongate members retain at least 15% of their initial strength, at least 30% of their initial strength, and/or at least 50% of their initial strength for 12 weeks following implantation.

In embodiments, the elongate members are designed to create new tissue planes in the breast that can be used to support a lifted breast as the elongate members degrade and lose strength. In embodiments, the elongate members are designed to distribute the load of the lifted breast over the area of the new tissue plane. Use of the elongate members to distribute the load of the breast provides a more durable result, and avoids concentration of the load, potential cheese wiring, and loss of tissue traction that can occur when only sutures are used in breast lift procedures. In this regard, the elongate members may be particularly desirable in lifting breasts with high fatty tissue contents where sutures tend to pull through the breast tissue. The elongate members spread the load of the lifted breast over an extended area.

In embodiments, the elongate member has a width between 0.2 to 5 cm, 0.4 to 2 cm, 0.8 and 1.5 cm, and/or any suitable range of widths. In embodiments, the elongate member has a length of between 10 to 85 cm, 25 to 63 cm, 25 and 47 cm, and/or any other suitable range of lengths. In embodiments, the elongate member has an average pore size of 0.01 to 4 $mm^2$ and/or 0.01 and 1 $mm^2$. In embodiments, the elongate member has a thickness from 0.25 to 2 mm, and/or between 0.4 and 1 mm.

In embodiments, the elongate member comprises at least one end terminating in a fused end, and in embodiments, the elongate member comprises at least one end terminating in a fused end wherein the fused end is perforated.

In embodiments, the elongate member is not anchored to the chest wall like other breast lift devices. In embodiments, the elongate member is not anchored to the circum-mammary ligament.

In embodiments, the elongate members are designed to support a load of at least 5 N, 10 N, 60 N, and/or any other suitable load less than 500 N.

In embodiments, the elongate member comprises a porous component. The porous component permits tissue in-growth.

In embodiments, the elongate members are sized for implantation through stab incisions made in the breast of the patient. In embodiments, the elongate members are designed for use without extensive dissection of the patient's tissue. In embodiments, the elongate members are designed for use without removal of the patient's tissue. In embodiments, the elongate members are designed for minimally invasive delivery. In embodiments, the elongate members are designed to be folded or rolled up, for example into a C-shape, prior to implantation in the patient. After implantation, the folded or rolled up elongate members may be deployed in the breast into their desired shapes. In embodiments, the elongate members have shape memory. After implantation, the elongate members with shape memory may be deployed in the breast into their desired shapes. In embodiments, the elongate members are designed to be implanted in channels formed in the breast, for example, by blunt dissection. In embodiments, the elongate members are designed to be implanted in channels formed in the breast with an introducer tool. In embodiments, the elongate members are designed to be implanted through one or more entry points at the IMF or in the lower pole of the breast. In embodiments, the elongate members are designed to be implanted through entry points in the lower pole of the breast.

In embodiments, the implants comprise an elongation member and one or more bioactive agents. Bioactive agents may be coated on the elongate members, or incorporated into the elongate members. Examples of bioactive agents include anti-microbials, antibiotics, proteins, and agents to promote tissue in-growth. In embodiments, the implant comprises an elongate member and one or more of the following: cells, stem cells, gels, hydrogels, fatty tissue, autologous fat, fat lipoaspirate, adipose cells, and fibroblast cells. These cells and materials may be coated onto the surfaces of the elongate members or incorporated into the body of the elongate members.

In embodiments, the elongate members have an endotoxin content of less than 20 endotoxin units.

In embodiments, the elongate members are sterile. In embodiments, the elongate members are sterilized with ethylene oxide, cold ethylene oxide, electron-beam irradiation, or gamma-irradiation.

In embodiments, the elongate members comprise resorbable polymers. In embodiments, the elongate members comprise one or more of the polymers listed in Section A. In some embodiments, the elongate members may include one or more of the following: poly-4-hydroxybutyrate or copolymer thereof, poly(butylene succinate) or copolymer thereof, or polydioxanone.

Fibers for Making Elongate Members of the Implants

In embodiments, the implants may comprise fibers. In embodiments, the elongate member may comprise fibers. The fibers may be made from resorbable thermoplastic polymers, and/or resorbable thermoplastic polyesters. The fibers may be made from the resorbable materials listed above. The fibers may be monofilament fibers, multifilament fibers, or combinations thereof. In some embodiments, the implants may comprise monofilament fibers. The fibers may be unoriented, partially oriented, oriented, highly oriented or combinations thereof. Oriented means that the fibers have been stretched. Stretching of the fiber causes molecular alignment of the polymer chains in the fiber, and increases the tensile strength of the fiber. ("Oriented" in this context does not relate to the geometry of a fiber in relation to another object.) The fibers may have elongation to break values of 3% to 120%, and/or 3% to 50%. In embodiments, the fibers may have diameters ranging from 1 micron to 5 mm, 10 microns to 1 mm, and/or 50 microns to 500 microns. The fibers may have weight average molecular weights ranging from 10 kDa to 1,200 kDa, and/or from 50 kDa to 600 kDa. The fibers may retain at least 50% of their initial strength in vivo for 1-6 months and/or for 2-4 months. The fibers may substantially degrade within 5 years of implantation, and/or within 2 years of implantation. The fibers may have initial tensile strengths ranging from 1 to 1.300 MPa, and/or from 50 MPa to 1,000 MPa.

In an embodiment, the implants or elongate members comprise fibers with one or more of the following properties: an elongation to break of 10-100%, and a tensile strength of 300-1,000 MPa.

In some embodiments, the elongate members of the implants comprise fibers made from P4HB. In some embodiments, the elongate members of the implants comprise fibers made from P4HB monofilament fiber. The P4HB monofilament fibers may be partially or fully oriented (i.e. partially or fully stretched after extrusion). In one embodiment, P4HB monofilament fiber may be produced according to the following method. Bulk P4HB resin in pellet form is dried to under 300 ppm water using a rotary vane vacuum pump system. The dried resin is transferred to an extruder feed hopper with nitrogen purge to keep the pellets dry. The pellets are gravity fed into a chilled feeder section and introduced into an extruder barrel, with a 1.5 inch (3.8 cm) diameter, and fitted with an extrusion screw with a 30:1 L/D ratio. The extruder barrel may contain 5 heating zones (or extrusion zones), and is manufactured by American Kuhne. The heated and softened resin from the extruder is fed into a heated metering pump (melt pump) and from the melt pump the extruded resin is fed into the heated block and an 8-hole spinneret assembly. Suitable processing profile ranges are from 40° C. to 260° C. for temperatures, and 400 psi to 2000 psi (2.76 MPa to 13.8 MPa) for pressures. The molten filaments may be water quenched and optionally conveyed into an orientation line, (e.g., a three-stage orientation line), and optionally with inline relaxation, before winding of the monofilaments on spools. This procedure may, for example, be used to produce P4HB monofilament fibers with one or more of the following properties: an elongation to break from 10-100%, a tensile strength from 50-1,300 MPa, and a tensile modulus from 70-1,000 MPa. The P4HB monofilament fibers may have average diameters ranging from 20 microns to 1 mm, and/or 50 microns to 500 microns. In an embodiment, the P4HB monofilament fibers may have USP (United States Pharmacopeia) absorbable suture sizes 10, 9, 8, 7, 6, 5, 4, 3, 2, 1, 0, 2-0, 3-0, 4-0, 5-0, 6-0, 7-0, 8-0, 9-0, 10-0, 11-0, and 12-0.

In another embodiment, the elongate members of the implants comprise fibers made from P4HB multifilament fiber. Multifilament fibers of P4HB or copolymers thereof may be spun, for example, as follows: The polymer, copolymer or blend thereof is pelletized, and dried so that the moisture content of the polymer, copolymer or blend is less than 300 ppm. The dried pellets are placed in the feed hopper of an extruder, and protected from moisture, for example with a dry nitrogen purge. The pellets are gravity fed into a chilled feeder section, and introduced into a suitable extruder barrel with an extrusion screw. One suitable extruder barrel has a diameter of 0.75 inches (1.91 cm) and length of 25.69 inches (65.3 cm), and is fitted with an extrusion screw with a 30:1 L/D ratio. American Kuhne makes a suitable extruder. In some embodiments, the extruder barrel contains 4 heating zones, and a processing profile is set with temperatures ranging from 40° C. to 300° C. and pressures of 200 psi to 3,000 psi (1.38 MPa to 20.7 MPa). The heated and softened polymer, copolymer or blend is fed into a metering pump, and from the metering pump the resin is fed into the heated block. The spin head is fitted with a spin pack comprising filtering media (screens), and spinnerets containing the desired number of holes for forming the individual filaments of the multifilament yarn. For example, the spinneret may have 15, 30, 60, 120 or more or less holes. The extruded filaments exit the spinneret, and pass through a heated chimney before they are allowed to cool. Spin finish may be applied to the multifilaments, and the multifilaments may either be collected on a winder, or oriented in-line. Suitable spin finishes include PEG400 and Tween 20™. The multifilament fiber may have a tenacity between 1 and 12 grams per denier. In embodiments, the multifilament fiber may be twisted to form a yarn. In embodiments, the elongate member comprises the yarn.

In some embodiments, the elongate members of the implants comprise fibers made from poly(butylene succinate) or copolymer thereof, and/or from monofilament fibers of poly(butylene succinate) or copolymer thereof. The monofilament fibers of poly(butylene succinate) or copolymer thereof may be partially or fully oriented (i.e. partially or fully stretched after extrusion). In one embodiment, monofilament fibers of poly(butylene succinate) or copolymer thereof may be produced according to the following method. Bulk resin is dried under vacuum overnight to less than 0.01% (w/w) water. Dried pellets of the polymer are fed under a blanket of nitrogen into the extruder barrel of a 2½" American Kuhne single screw extruder (30:1 L:D, 3:1 compression) equipped with a Zenith type metering pump model HPB917, a die with 0.5 mm-8 hole spinneret and 8 heat zones. The 8 heating zones of the extruder are set between 40° C. and 200° C. The extruder is fitted with a quench bath filled with water at 35-70° C. and set up with an air gap of 10 mm between the bottom of the spinneret and the surface of the water. Two 5-roll godets are positioned after the quench bath, followed by three sets of hot conduction chambers fed by godets in order to orient the fiber in multiple stages. The temperatures of the hot chambers are set between 50° to 90° C. temperature. Another godet is positioned after the last chamber, and then a multi-position Sahm winder. This procedure may, for example, be used to produce monofilament fibers of poly(butylene succinate) or copolymer thereof with one or more of the following properties: an elongation to break from 10-100%, and/or 10-50%, a tensile strength from 50-1,300 MPa, and/or 400-1,200 MPa, and a tensile modulus from 50-3,000 MPa. The monofilament fibers of poly(butylene succinate) and copolymers thereof may have average diameters ranging from 20 microns to 1 mm and/or 50 microns to 500 microns. In an embodiment, the monofilament fibers of poly(butylene succinate) or copolymers thereof may have USP (United States Pharmacopeia) absorbable suture sizes 10, 9, 8, 7, 6, 5, 4, 3, 2, 1, 0, 2-0, 3-0, 4-0, 5-0, 6-0, 7-0, 8-0, 9-0, 10-0, 11-0, and 12-0.

In another embodiment, the elongate members of the implants comprise multifilament fiber made from poly(butylene succinate) and copolymers thereof. The multifilament fibers of poly(butylene succinate) or copolymer thereof may be partially or fully oriented (i.e. partially or fully stretched after extrusion). In one embodiment, the multifilament fibers of poly(butylene succinate) or copolymer thereof may be produced according to the following method. Bulk resin is dried under vacuum to less than 0.01% (w/w) water. Dried pellets of the polymer are fed into an extruder barrel of an AJA (Alex James Associates, Greer, S.C.) ¾" single screw extruder (24:1 L:D). The extrusion barrel contained 4 heating zones, a metering pump and a spin pack assembly. The pellets are gravity fed into a chilled feeder section and introduced into the extruder with temperature profile set as follows: Chimney 40° C.-100° C., Spinneret 170° C.±30° C., Pump 170° C.±30° C., Block 170° C.±30° C., Zone 4 160° C.±40° C., Zone 3 150° C.±40° C., Zone 2 120° C.±50° C., Zone 1 30° C.-40° C., Feed Zone: Ambient temperature. The heated and homogenized melted resin from the extruder is fed into a heated metering pump (melt pump), and from the melt pump the extruded resin is fed into the heated block and the spinneret assembly. The spinneret has 30 holes with a capillary diameter of 0.200 millimeters and a L/D ratio of 2:1. (The spinneret may also be configured in other alternative manners. For example, the spinneret can be configured with capillary diameters from 0.150 to 0.300 millimeters (6 mil to 12 mil) and 15, 120 and 240 holes, as well as higher and lower diameters and numbers of holes.) Suitable processing temperature profile ranges are from 35° C. to 250° C. with pressures ranging from 200 to 5,000 psi (1.38 MPa to 34.5 MPa) in the barrel and 200 to 5,000 psi (1.38 MPa to 34.5 MPa) in the spin pack. As the molten filaments exit the spin pack, they pass through a heated chimney collar that is 6-12 inches long and range in temperature from 40° C. to 100° C., and then through an air quench box. The spin pack is suspended vertically above a yarn take-up roll at a distance sufficient to allow crystallization of the molten filaments and application of spin finish lubricant. A spin finish solution of 25% polyethylene 25 glycol 400 (PEG400) in water is used to hold the filaments together to form a yarn bundle. The speed of the yarn take-up rolls (typically 3-18 meters per minute) is set in proportion to the flow rate of the molten filament to control the denier of the as spun yarn bundle. The as spun yarn bundle is then conveyed to a Lessona winder for offline later orientation or conveyed to a take-up roll for inline orientation on a series of cold and heated godet pairs and separator rolls. If desired, the spin finish can be reactivated by rewetting the yarn bundle with pure water, and the yarn drawn at ratios from 5 to 14× and temperatures ranging from 50° C. to 90° C. This procedure may, for example, be used to produce multifilament fibers of poly(butylene succinate) or copolymer thereof with one or more of the following properties: an elongation to break from 10-100% and/or 10-50%, and a tenacity greater than 1 gram per denier, and/or greater than 4 grams per denier, but, in some embodiments, less than 14 grams per denier.

Textiles or Fabrics for Preparing the Elongate Members of the Implants

In embodiments, the elongate members comprise textiles or fabric. Textiles or fabric include mesh, braids, woven mesh and knitted mesh. The textiles may comprise resorbable fibers, including, but not limited to resorbable monofilament fibers. In embodiments, the resorbable monofilament fibers are polymeric and oriented. Oriented in this embodiment means that the fibers have been stretched to increase the molecular alignment of the polymer chains in the fibers.

The fibers described above may be processed into textiles, for example, by knitting, stitching, weaving, or crocheting, and used to form the elongate members. An exemplary textile for preparing the elongate member of the implant is a two loop pillar construction. Another exemplary textile for use in preparing the elongate member of the implant is a mesh, a warp knit mesh, and/or a resorbable warp knit mesh.

In embodiments, textiles used to prepare the elongate members of the implants have burst strengths between 0.6 and 90 N/cm$^2$, and/or between 1.2 and 30 N/cm$^2$. In embodiments, textiles used to prepare the elongate members of the implants may have one or more of the following properties: burst strengths between 0.1 to 100 kg, 1 to 50 kg. 5-100 kg, 10 to 50 kg, and/or any other suitable burst strength, (i) a suture pullout strength of at least 1 kgf, (ii) a burst strength of 0.1 to 100 kg. (iii) a thickness of 0.05-5 mm, 0.1 to 1 mm, 0.1 to 0.5 mm, and/or any other suitable thickness, (iv) an areal density of 5 to 800 g/m$^2$, 10 to 1000 g/m$^2$, 20 to 500 g/m$^2$, 5 to 1000 g/m$^2$, 10 to 100 g/m$^2$, 200 to 800 g/m$^2$, and/or any other suitable areal density, and (v) a pore diameter of 5 μm to 10 mm, 10 μm to 1 mm, 100 μm to 10 mm, 10 μm to 100 μm, and/or any other suitable pore diameter. In some embodiments, the elongation member of the implant comprises a textile, and the textile may have one or more of the following properties: (i) a suture pullout strength of 1 kgf to 20 kgf, (ii) a burst strength of 1 to 50 kg or 10 to 50 kg. (iii) a thickness of 0.1 to 1 mm, (iv) an areal density of 100 to 300 g/m$^2$, and (v) a pore diameter of 100 μm to 1 mm.

In embodiments, textiles used to prepare the elongate members of the implants have burst strengths 3 months after implantation of at least 40% of their initial burst strength values.

In embodiments, textiles used to prepare the elongate members of the implants are porous, and can be replaced in vivo by host tissue growing into and around the textiles that is strong enough to support the breast lift. The diameters of the implant's pores or pores in the textile may be larger than 25 μm, 75 μm, and/or 250 μm in order to facilitate tissue in-growth, but may be smaller than 20 mm, 10 mm, and/or 5 mm.

Elongate members of implants comprising textiles, such as knitted and woven meshes, and two loop pillar construction textiles, may be produced using fibers of P4HB or copolymer thereof, and or fibers of poly(butylene succinate) or copolymer thereof. The fibers may be monofilament fibers. Elongate members of the implants comprising oriented or partially oriented monofilament fibers of these polymers and copolymers have a prolonged strength retention profile, and can maintain some residual strength for as much as one year. The prolonged strength retention of these fibers provides an extended period for tissue in-growth into textiles made from these fibers. Tissue in-growth into these textiles leads to the formation of a new tissue plane in the breast that can support a breast lift. Moreover, the prolonged strength retention of the fibers and textiles means that mastopexy implants comprising these fibers and textiles can provide short-term support for the lifted breast while the new tissue plane develops in the breast.

In other embodiments, the elongate members of the implants comprising textiles, including two loop pillar constructs, or knitted meshes, may be produced using fibers of polydioxanone, for example, monofilament fibers of polydioxanone, and/or oriented monofilament fibers of polydioxanone.

A suitable knitted P4HB mesh for preparing the elongate members of the implants may be prepared, for example, by the following method. Monofilament fibers of P4HB from 49 spools are pulled under uniform tension to the surface of a warp beam. A warp is a large wide spool onto which individual fibers are wound in parallel to provide a sheet of fibers ready for coating with a 10% solution of Tween® 20 lubricant. Tween 20 lubricant is added to the surface of the sheet of fiber by means of a 'kiss' roller that is spinning and is immersed in a bath filled with Tween 20. The upper surface of the roller is brought into contact with the sheet of fiber, and the roller spun at a uniform speed to provide a consistent application of Tween 20 finish. Following the application of Tween 20, the sheet of fiber is placed onto a creel position such that each spooled fiber is aligned and wrapped side by side to the next spooled fiber on a warp beam. Next, warp beams are converted into a finished mesh fabric by means of interlocking knit loops. Eight warp beams are mounted in parallel onto a tricot machine let-offs and fed into the knitting elements at a constant rate determined by the 'runner length'. Each individual monofilament fiber from each beam is fed through a series of dynamic tension elements down into the knitting 'guides'. Each fiber is passed through a single guide, which is fixed to a guide bar. The guide bar directs the fibers around the needles forming the mesh structure. The mesh fabric is then pulled off the needles by the take down rollers at a constant rate of speed. The mesh fabric is then taken up and wound onto a roll. The P4HB monofilament mesh produced according to this method may be scored ultrasonically with water, optionally heat set in hot water, and optionally washed with a 70% aqueous ethanol solution.

In embodiments, textiles (including meshes) made from P4HB monofilaments that may be used to prepare the implants have one or more of the following properties: (i) a suture pullout strength of at least 1 kgf. (ii) a burst strength of 0.1 to 100 kg, (iii) a thickness of 0.05-5 mm, (iv) an areal density of 5 to 800 g/m$^2$, and (v) a pore diameter of 5 μm to 5 mm. In embodiments, the P4HB textiles, including the monofilament P4HB meshes, have one or more of the following properties: (i) a suture pullout strength of 1 kgf to 20 kgf, (ii) a burst strength of 1 to 50 kg and/or 10 to 50 kg. (iii) a thickness of 0.1 to 1 mm, (iv) an areal density of 100 to 300 g/m$^2$, and (v) a pore diameter 100 μm to 1 mm. In embodiments, the P4HB monofilament mesh or P4HB textile has substantially one or more of the following properties: a pore diameter of 500±100 μm, a thickness of 0.5±0.2 mm, an areal density of approx. 182±50 g/m$^2$, a suture pullout strength of 5.6±2 kgf, and a burst strength of at least 15 kg and/or at least 24.5 kg.

A suitable knitted mesh of poly(butylene succinate) or copolymer thereof for use in the implants may be prepared, for example, by the following method. Monofilament fibers from 49 spools are mounted on a creel, aligned side by side and pulled under uniform tension to the upper surface of a "kiss" roller. The "kiss" roller is spinning while semi-immersed in a bath filled with a 10% solution of polyethylene glycol sorbitan monolaurate, polyethylene glycol, or other suitable lubricant. The lubricant is deposited on the surface of the sheet of fiber. Following the application of the lubricant, the sheet of fiber is passed into a comb guide and then wound on a warp beam. A warp is a large wide cylinder onto which individual fibers are wound in parallel to provide a sheet of fibers. Next, warp beams are converted into a finished mesh fabric by means of interlocking knit loops. Eight warp beams are mounted in parallel onto tricot machine let-offs and fed into the knitting elements at a constant rate determined by the 'runner length'. Each individual monofilament fiber from each beam is fed through a series of dynamic tension elements down into the knitting 'guides'. Each fiber is passed through a single guide, which is fixed to a guide bar. The guide bar directs the fibers around the needles forming the mesh fabric structure. The mesh fabric is then pulled off the needles by the take down rollers at a constant rate of speed determined by the fabric 'quality'. The mesh fabric is then taken up and wound onto a roll ready for scoring. The poly(butylene succinate) or copolymer thereof monofilament mesh is then scoured ultrasonically with water, and may be (i) heat set (for example in a hot conductive liquid bath or an oven), and then (ii) washed with a 70% aqueous ethanol solution.

Meshes and other textiles, including a two loop pillar construct, made from monofilaments or multifilaments of poly(butylene succinate) or copolymers thereof suitable for preparing the implants may have one or more of the following properties: (i) a suture pullout strength of at least 10 N, or at least 20 N, (ii) a burst strength of 0.1 to 100 kgf and/or between 1 to 50 kgf, or greater than 0.1 kPa, (iii) a thickness of 0.05-5 mm, (iv) an areal density of 5 to 800 g/m$^2$, (v) a pore diameter of 5 μm to 5 mm and/or 100 μm to 1 mm, and (vi) Taber stiffness of at least 0.01 Taber Stiffness units and/or 0.1-19 Taber Stiffness units. In some embodiments, these monofilament or multifilament meshes and other textiles have one or more of the following properties: (i) a suture pullout strength of 1 kgf to 20 kgf, (ii) a burst strength of 1 to 50 kgf and/or 5 to 30 kgf, (iii) a thickness of 0.1 to 1 mm, (iv) an areal density of 100 to 300 g/m$^2$, and (v) a pore diameter of 100 μm to 1 mm. In other embodiments, the monofilament or multifilament mesh or other textile of poly(butylene succinate) or copolymer thereof suitable for preparing the elongate member of the implants has substantially one or more of the following properties: a pore diameter of 500±100 μm, thickness of 0.4±0.3 mm, areal density of approx. 182±50 g/m$^2$, suture pullout strength of 5.6±2 kgf, and a burst strength of at least 3 kgf, and/or at least 6 kgf.

Films for Forming the Elongate Members

The elongate members may comprise a film or laminate. In some embodiments, the film or laminate may be porous to permit tissue ingrowth. The elongate members may be formed from the polymers described above, including, for example, resorbable polymers.

In embodiments, the film or laminate comprises P4HB or copolymer thereof. These polymers may be converted into a film by any suitable method, including extrusion, solvent casting, injection molding and compression molding.

In some embodiments, a method the film comprising P4HB or copolymer thereof is extruded either directly from a powder or granular form, or from pellets. The polymer may be dried prior to extrusion. Melt-extrusion may be used to prepare films of P4HB, suitable for preparing elongate members, using barrel and T-die temperatures, for example, of 80 to 250° C., and/or 100 to 220° C. In an embodiment, the molten P4HB film exiting the T-die is chilled by casting it over one or more rotating cylindrical cast rollers with a surface temperature of 5 to 100° C. and/or 5 to 20° C. The solidified film may then be wound up in a take up step to collect the film. Films of P4HB suitable for forming the elongate member with different thicknesses can be produced using this process by adjusting the gap of the T-die slit, and altering the polymer flow rate and cast roll speed.

Films of P4HB or copolymer thereof suitable for forming the elongate member may also be prepared by extrusion using an inflation method wherein an inflation molding circular die is used instead of a T-die to extrude cylindrical film. After exiting the circular die, the molten cylindrical film is cooled by blowing it up using cold air blown from the central portion of the circular die. Once the polymer has solidified, the film may be collected using a take-up machine. P4HB films of different thicknesses can be produced by changing the gap of the inflation die slit, as well as altering the polymer flow rate, cooling air pressure, temperature of the air, and the take-up speed.

Suitable films of P4HB and copolymers thereof for forming the elongate members may also be made by compression molding. In one embodiment, compositions including P4HB may be pressed into films using a Carver hydraulic press. In some embodiments, compositions including P4HB powder, granules or pellets may be pressed into films by heating the platens of the press to 115° C., and pressing the P4HB composition between two sheets of mylar using metal spacers. After pressing, the film is removed from the press, allowed to cool and solidify, and removed from the mylar backing material. The thickness of the metal spaces may be adjusted in order to produce films of the desired thickness.

Suitable films of P4HB and copolymers thereof for forming the elongate members may also be prepared by solvent casting. In some embodiments, a solution of P4HB may be prepared by dissolving the P4HB polymer in a solvent at a concentration of 10-15 wt/vol %, or at a concentration such that the P4HB solution has a viscosity of 400 to 7,400 cP. Suitable solvents include tetrahydrofuran, 1,4-dioxane, acetone, chloroform, and methylene chloride. The polymer solution may be pumped through a slot die onto a moving web such as, for example, an aluminum foil. The distance traveled by the moving web before being taken up on a collection roller may be adjusted to ensure evaporation of the solvent, and one or more air-drying zones, (e.g., with elevated temperatures), may be used to speed up solvent evaporation. In one embodiment, the slot die has a width of 150 mm and a 400 μm die gap, and the web speed is 0.5 m/min with the web traveling 5 m before the film is collected on a final roll. The pump speed, die gap and width, polymer concentration, and web speed may all be varied to produce P4HB films of the desired thickness and widths for forming the elongate member.

The films of P4HB or copolymer thereof may be oriented. Suitable methods to orient films of P4HB or copolymer thereof include roll stretching and/or stretching with a tenter frame. In some embodiments, the films may be stretched at a temperature between room temperature and 150° C., and/or at 40 to 80° C., and with a stretch ratio of 0.25 to 15. The films may be monoaxially stretched to form monoaxially-oriented films, consecutively stretched in biaxial directions to form biaxially oriented films, or simultaneously biaxially stretched to form plane-oriented films.

In an embodiment, the oriented film of P4HB or copolymer thereof can be heat set. Films of P4HB may be heat set by restraining the films at the desired stretched dimensions, and heating to a temperature of less than 60° C., and/or between 35 to 45° C.

In some embodiments, the film of P4HB or copolymer thereof for forming the elongate member is porous or fibrillated. These films can be made by mechanical or laser drilling, punching or any similar method to create pores in the film.

In embodiments, the film or laminate for preparing the elongate member comprises a polymeric composition, comprising a 1,4-butanediol unit and a succinic acid unit as described herein or copolymer thereof. These polymers may be converted into a film by any suitable method, including extrusion, solvent casting, injection molding and compression molding.

In embodiments, a film of PBS polymer or copolymer thereof for forming the elongate member may be prepared by solution casting as follows. A homogeneous solution of PBS polymer or copolymer in a suitable solvent is prepared. The polymer solution is pumped through a slot die with a suitable die gap onto a moving web, for example, of aluminum foil. The web speed may, for example, be approximately 0.5 m/min and it may travel 5 m before being collected on a collection roller. The speed is adjusted to ensure evaporation of the solvent. One or more separate air drying zones set at a suitable temperature are employed to remove solvent from the polymer film before collection on the final roll. A number of parameters can be varied to control the film thickness including, but not limited to, the pump speed, the die gap and width, the polymer concentration and the web speed.

In embodiments, a film of PBS polymer or copolymer thereof for forming the elongate member may be prepared by melt-extrusion methods. Exemplary methods include a T-die extrusion method or an inflation method. In the formation of the film by melt-extrusion, suitable barrel and T-die temperatures for carrying out the formation are selected to ensure melting of the PBS polymer or copolymer thereof but not so high as to cause unacceptable thermal decomposition. However, the site of the barrel directly below a hopper may have a temperature of less than the melting temperature of the PBS polymer or copolymer thereof. The molten film exits the T-die and may be cast over a chilled moving surface, one or more rotating cylindrical cast rollers with surface temperature maintained at a temperature of less than the melting temperature of the PBS polymer or copolymer thereof. This step is followed by a take-up step to wind up the extruded film. Film thickness can be varied by changing the gap of the T-die slit, polymer flow rate, and cast roll speed.

In embodiments, a film of PBS or copolymer thereof for forming the elongate member is extruded by a process comprising the following steps: (i) drying the PBS polymer or copolymer thereof to a moisture content of less than 0.01 wt % water; (ii) feeding the dried polymer or copolymer into an extruder barrel with a film extrusion die, wherein the heating zones of the extruder and the die are set at temperatures between 60° C. and 240° C. and/or between 70° C. and 220° C., and (iii) casting the extrudate on a chilled roll stack set at a temperature below the melt temperature of the PBS polymer or copolymer, including, but not limited to a temperature between 5° C. and 50° C.

In the formation of a film of PBS or copolymer thereof by the inflation method, an inflation molding circular die is used instead of a T-die to extrude cylindrical films. The molten cylindrical film is cooled and solidified by blowing it up with cold air blown from the central portion of the circular die, and the cylindrical film which had been blown up is collected with a take-up machine. Film thickness can be varied by changing the gap of the inflation die slit, polymer flow rate, cooling air pressure and temperature and take-up speed.

Films formed from PBS polymer or copolymer thereof, such as the melt-extrusion films and solvent cast films, may be oriented by stretching using any suitable method including roll stretching and/or a stretching method using a tenter frame. The melt-extruded PBS film, for example, can be stretched at a stretch ratio of 0.25 to 15. The stretching may be monoaxial stretching for forming a monoaxially oriented film, consecutive biaxial stretching for forming a biaxially oriented film and simultaneous biaxial stretching for forming a plane-oriented film.

Sheaths to at Least Partially Cover Elongate Members

In embodiments, the elongate member of the implant is partially or totally inserted inside one or more removable sheaths for delivery of the elongate member to the implant site. All or part of the elongate member may be inserted inside one or more sheaths in order to facilitate delivery of the elongate member to the implant site. In particular, one or more removable sheaths may be used to prevent the elongate member from engaging breast tissue prematurely during implantation, and particularly before the elongate member is located in the desired position in the breast. In embodiments, the elongate member is partly or fully inserted inside a removable sheath, the sheath comprising the elongate member is implanted in the breast, and the removable sheath is removed from the breast to deploy the elongate member in the breast. In embodiments, the elongate member may be at least partly covered by a single sheath. In embodiments, the elongate member may be at least partly covered by two or more sheaths. In embodiments, the sheath may be a continuous tube or comprise sections where the elongate member remains exposed. In embodiments, the sheath may comprise a tear region. The tear region allows the sheath to be torn at a specific location.

In embodiments, the removable sheath comprises a polymer. In embodiments, the sheath is formed from nylon, high density polyethylene, polytetrafluoroethylene and low density polyethylene.

Tensioner

In embodiments, the mastopexy system further comprises a tensioner. The tensioner is designed to increase or decrease the tension of the elongate member on the breast tissue, and allow adjustment of the breast lift.

Examples of tensioners include a pulley system, or a spool tensioner. In embodiments, the tensioner may be adjusted during implantation, or the tensioner may be adjusted after implantation, for example, to apply more tension to the elongate member to lift the breast. In embodiments, the tensioner may be adjusted using a small tool that is inserted through a small incision.

In embodiments, the tensioner may be incorporated in the elongate member of the implant, and/or incorporated at the first or second ends of the elongate member.

In embodiments, the tensioner comprises an absorbable polymer. In embodiments, the tensioner comprises one or more polymers listed in Section A. In some embodiments, the tensioner may include one or more of the following: poly-4-hydroxybutyrate or copolymer thereof, poly(butylene succinate) or copolymer thereof, or polydioxanone.

Fastening Anchors

In embodiments, the implant of the mastopexy system comprises one or more, or optionally two fastening anchors to secure the elongate member in place after the breast has been lifted. In embodiments, the fastening anchor comprises a feature to allow the fastening anchor to be sutured to tissue. In embodiments, the fastening anchor has a T-shape. In embodiments, the fastening anchor has a T-cap pin. In embodiments, the T-cap pin has a suture hole sized to pass suture.

In embodiments, the fastening anchor has two arms. The arms are connected at one end to the elongate member, and to opposite ends of the T-cap pin at the other end of the arms. In embodiments, the T-cap pin is formed by injection molding. In embodiments, the arms are formed from monofilament fibers, including, but not limited to, P4HB monofilament fibers.

Introducer Tools

The implant comprising the elongate member is designed to be implanted using one or more introducer tools. The elongate member may be at least partly covered by one or more sheaths, and delivered to the desired location in the breast using one or more introducer tools.

In embodiments, the introducer tool has a handle. In embodiments, the handle is made from medical grade polypropylene. In embodiments, the handle may be 10-15 cm, and/or 12 cm in length, and may have a diameter of 2-3 cm, and/or 2.5 cm. In embodiments, the introducer tool has a universal handle design to allow for both left- and right-handed use.

In embodiments, the introducer tool comprises an introducer needle. In embodiments, the introducer needle is made from 316L stainless steel. In some embodiments, the introducer needle comprises a tubular section with an inlet opening for insertion of the elongate member or an assembly of the elongate member at least partly covered by the sheath.

In embodiments, the introducer tool further comprises a detachable barrel tip. In embodiments, the detachable barrel tip is made from 316L stainless steel.

Methods for Preparing Mastopexy Implants and Systems for Mastopexy

A variety of methods can be used to manufacture the mastopexy implants and systems for mastopexy. In some embodiments, the mastopexy implants are resorbable, and are designed to support the mechanical forces acting on the breast during normal activities at the time of implantation, and to allow a steady transition of mechanical forces to regenerated host tissues that can also support those same mechanical forces once the implant has degraded.

Mastopexy Systems

In embodiments, the mastopexy systems comprise: (i) an implant comprising an elongate member, (ii) one or more sheaths at least partly covering the implant that are used to deliver the implant to the implantation site and are then removed from the breast, and (iii) one or more introducer tools for implanting the implant covered by the one or more sheaths. In embodiments, the mastopexy system comprises an assembly of an elongate member at least partly covered by one or more sheaths, and one or two introducer tools, wherein the introducer tools are loaded with an assembly of the elongate member at least partly covered by one or more sheaths.

FIGS. 3-9 show embodiments of components of the mastopexy systems, the design of components, and how systems for minimally invasive mastopexy may be assembled from the components.

Figure 3:
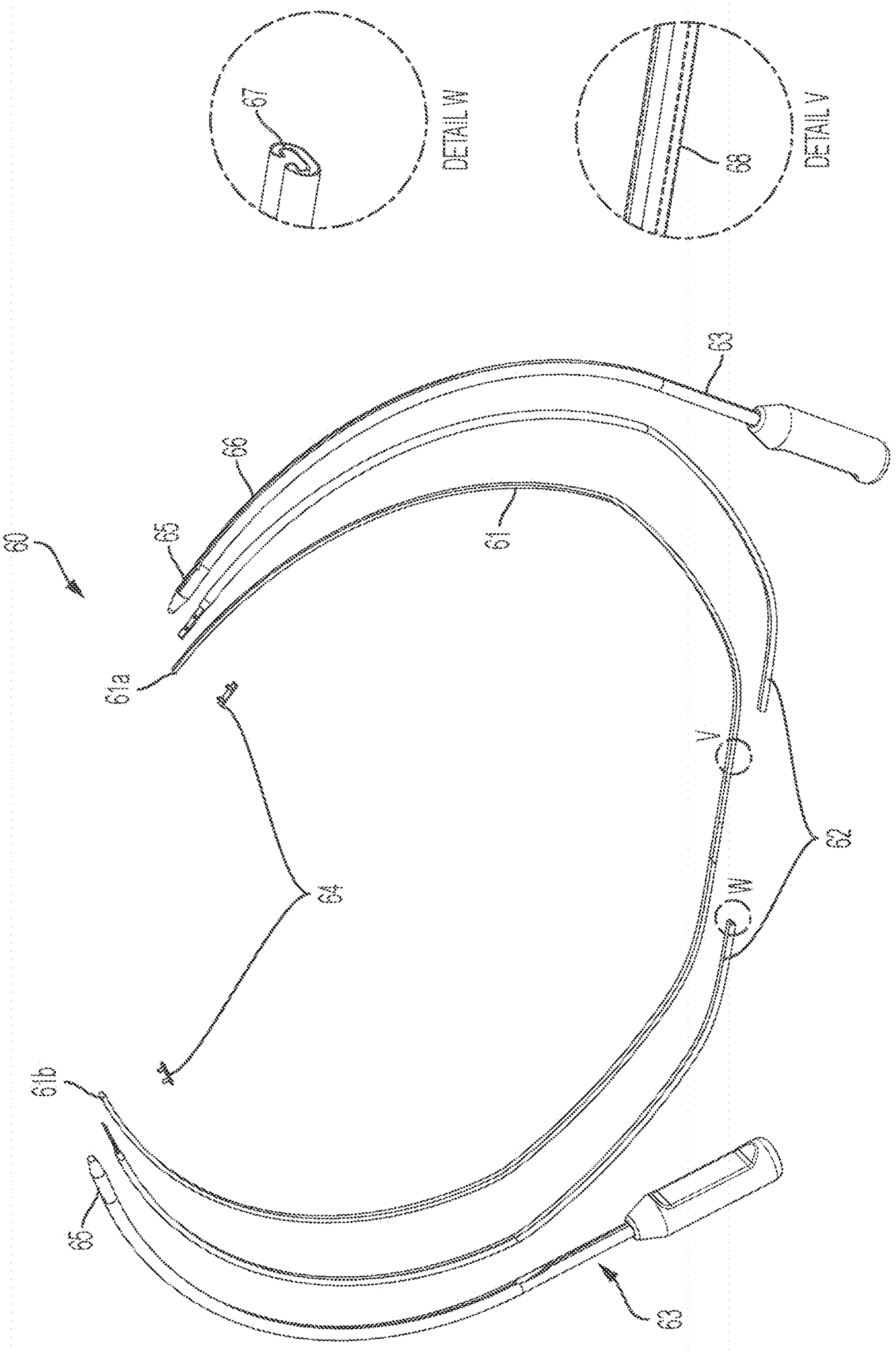
FIG. 3 shows an exploded view of an exemplary system 60 for mastopexy. The assembled view of this system is shown in FIG. 1. The system shows an elongate member 61 with a first end 61*a* and a second end 61*b*, two sheaths 62, two introducer tools 63, and latches 64 for connecting the assembly of the elongate member 61 and sheath 62 to the detachable barrel tip 65. Detail W in FIG. 3 shows a view of the C-shaped cross-section 67 of the sheath 62. Detail V in FIG. 3 is an enlarged view of the elongate member 61 showing the porous structure 68 of the elongate member.

FIG. 3 shows an illustrative system for mastopexy in accordance with one embodiment of the invention. FIG. 3 shows an exploded view 60 of the assembled mastopexy system shown in FIG. 1. The mastopexy system comprises the elongate member 61 of the implant, sheath 62 that covers the elongate member 61 at least partly, introducer tools 63, and latches 64 that are used to connect the assembly of the elongate member 61 and sheath 62 to the detachable barrel tips 65. The elongate member 61 has a first end 61*a* and a second end 61*b*. The assembly of the elongate member 61 and sheath 62 are shown rolled into a C-shape in order to insert the assembly into the tubular section 66 of the introducer tool 63. Detail W in FIG. 3 shows the C-shaped cross-section 67 of the sheath 62. The elongate member may be porous. A porous elongate member may encourage tissue ingrowth into the structure of the elongate member. Detail V in FIG. 3 shows the porous structure 68 of the elongate member 61.

Figure 4:
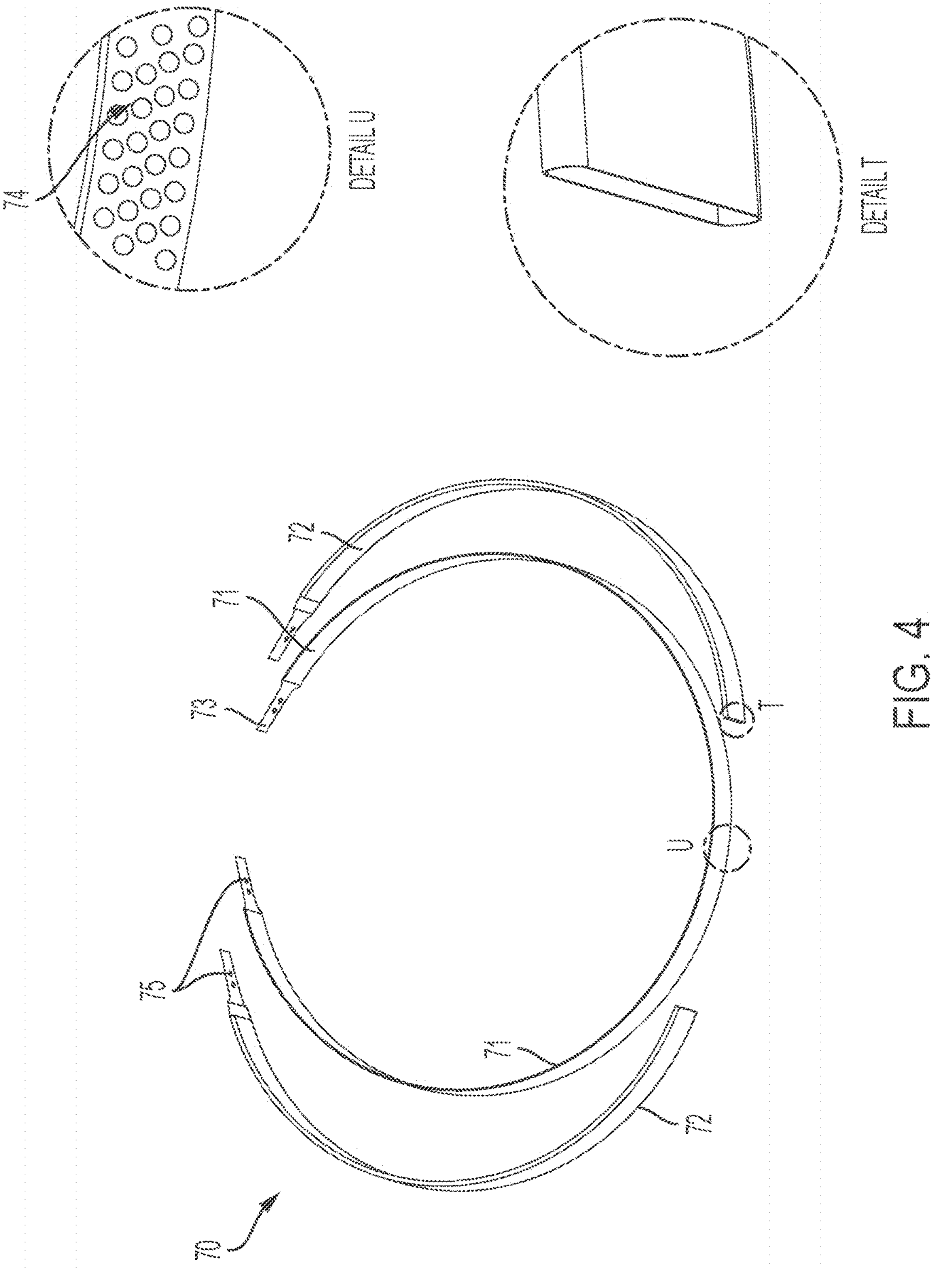
FIG. 4 shows an exploded isometric view 70 of an assembly of an elongate member 71 and a sheath 72.

Further details of the embodiment of the mastopexy system shown in FIG. 3 are provided in FIG. 4. FIG. 4 shows an exploded isometric view 70 of the assembly of the elongate member 71 of the implant and a sheath 72. In FIG. 4, the elongate member 71 and sheath 72 comprise fused ends 73. In embodiments, the mastopexy system is formed by placing the elongate member 71 of the implant at least partly inside the sheath 72, and fusing the ends of the elongate member and sheath together to form an assembly. The assembly is then inserted in the tubular section of an introducer tool to form a system for minimally invasive mastopexy. Detail T in FIG. 4 shows the cross-sectional structure of sheath 72 that is designed to receive the elongate member 71. Detail U in FIG. 4 shows an exemplary embodiment where the elongate member is porous 74. In embodiments, the fused ends 73 of the assembly of the elongate member and sheath comprise perforations 75. The perforations 75 are made in order to form an attachment feature for connecting the assembly of the elongate member and sheath to the detachable barrel tip of the introducer tool. The perforations 75 are sized to allow the assembly of the elongate member and sheath to be latched to the detachable barrel tip of the introducer tool using a latch with pins that are passed through the perforations.

Figure 5:
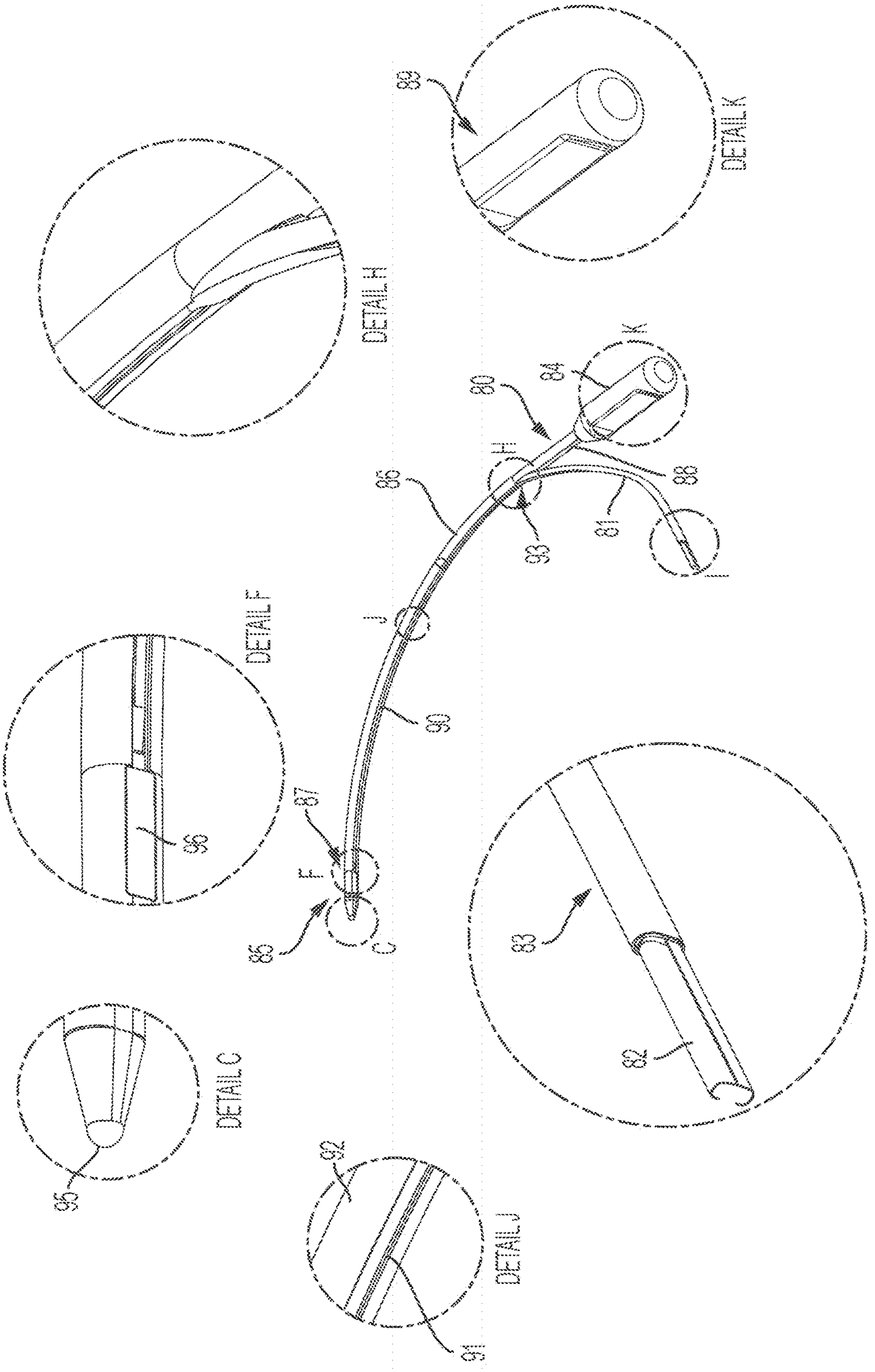
FIG. 5 shows an introducer tool 80 loaded with an assembly 81 of an elongate member enclosed in a sheath. Detail I is an enlarged view of the cross-section of the assembly 81 showing the elongate member 82 and sheath 83. The introducer tool 80 is shown with a handle 84, detachable barrel tip 85, and a tubular section 86 with a first end 87 and a second end 88. The first end 87 of the tubular section 86 is shown connected to the detachable barrel tip 85, and the second end 88 of the tubular section 86 is shown connected to the handle 84. Detail K shows an enlarged view 89 of the handle with a universal grip. A slit 90 is shown in the tubular section of the introducer tool 80 dimensioned to allow insertion and removal of assembly 81. Detail J is an enlarged view of the tubular section of the introducer tool showing the slit 91 and the tubular section 92. An inlet opening 93 on the introducer tool 80 is shown where the assembly 81 is inserted into the tubular section 86 of the introducer tool 80. Detail H is an enlarged view of the inlet opening 93 with the assembly of the elongate member and sheath inserted through the inlet opening. Detail C is an enlarged view of the cutting edge 95 of the detachable barrel tip. Detail F is an enlarged view of the latch receptacle 96 of the detachable barrel tip sized to receive an attachment feature (not shown) formed by fusion of an end of the assembly of the elongate member and sheath.

In embodiments, the introducer tool 80 of the mastopexy system comprises assembly 81 of the elongate member and sheath as shown in FIG. 5 at least partly loaded into the introducer tool. An enlarged view of the assembly of the elongate member 82 and sheath 83 is shown in Detail I. In the embodiment shown in FIG. 5, the introducer tool 80 comprises a handle 84, a detachable barrel tip 85, and a tubular section 86 with a first end 87 that connects to the detachable barrel tip 85, and a second end 88 that connects to the handle 84.

An enlarged view of the handle 89 is shown in Detail K. The handle 89 of the introducer may have a universal grip designed for right or left handed use. In embodiments, at least part of the tubular section comprises a slit 90 as shown in FIG. 5.

Detail J shows an enlargement of the tubular section of the introducer tool showing slit 91 in the tubular section 92. The slit 90 is dimensioned to allow insertion and removal of the assembly 81 of the elongate member and sheath inside the tubular section. In embodiments, the introducer tool comprises an inlet opening 93 in the tubular section of the introducer tool positioned to allow insertion of the assembly 81 of the elongate member and sheath inside the tubular section 86.

An enlarged view of the inlet opening 93 is shown in Detail H. In embodiments, the detachable barrel tip 85 comprises a blunt dissection tip 95 as shown in enlargement Detail C. In embodiments, the detachable barrel tip 95 is fitted with a sharp tip instead of a blunt dissection tip. In embodiments, the detachable barrel tip 85 comprises a latch receptacle 96 shown in an enlarged view in Detail F in FIG. 5. The latch receptacle 96 is designed to receive an attachment feature formed by fusion of the elongate member and sheath, and subsequent perforation of the fused area.

Figure 6:
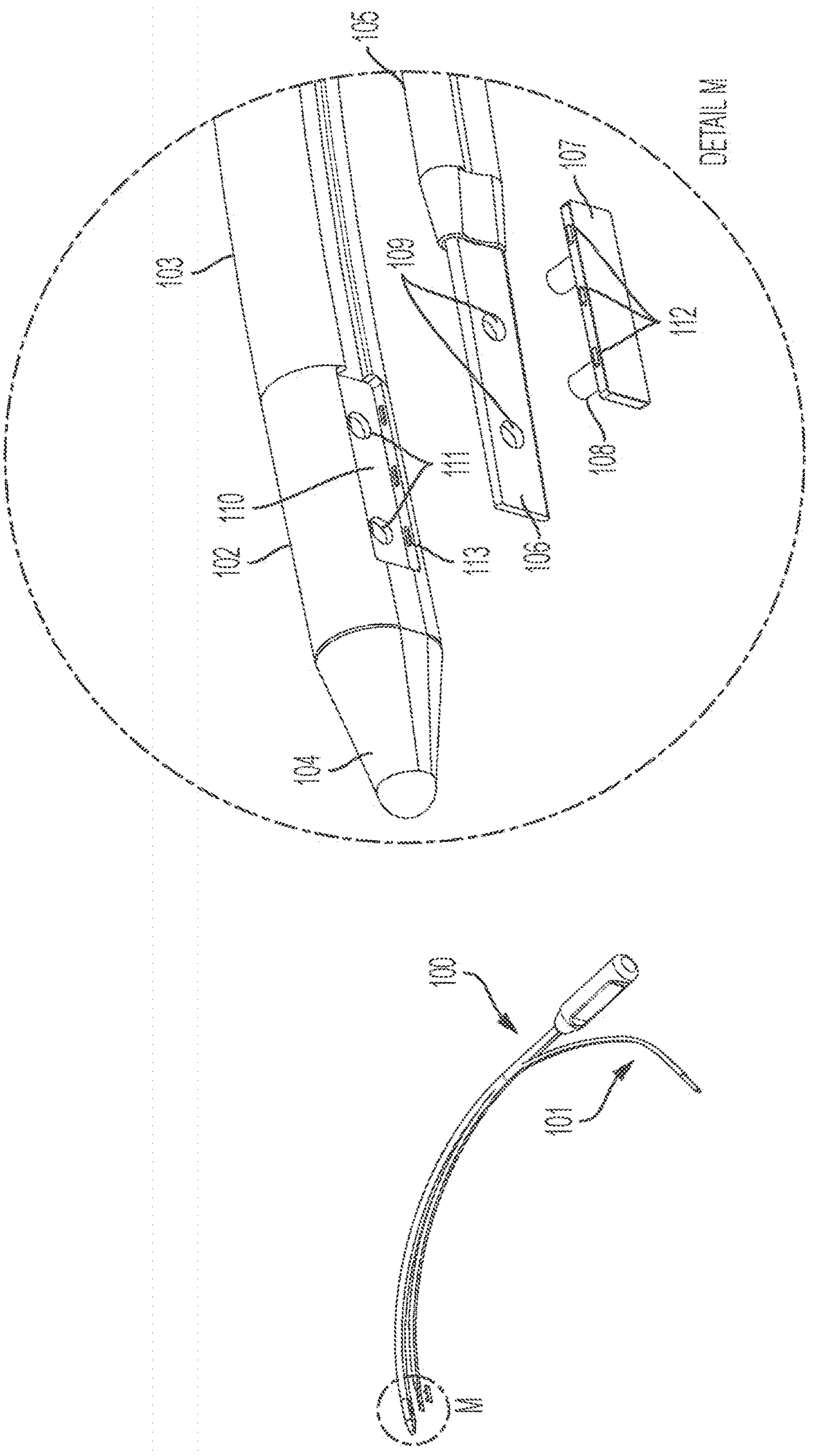
FIG. 6 shows an exploded isometric view of an introducer tool 100 loaded with an assembly 101 of an elongate member and sheath. Detail M shows an enlarged view of the detachable barrel tip 102 attached to the first end 103 of the tubular section of the introducer tool, and a sharp cutting edge 104 of the detachable barrel tip. Detail M also shows the assembly 105 of the elongate member and sheath terminating in an attachment feature 106 formed by fusing the elongate member and sheath together, and a latch 107 with lock pins 108 sized to pass through the perforated holes 109 of the attachment feature 106. The detachable barrel tip 102 is shown with a latch receptacle 110 containing two recessed holes 111 sized to receive the lock pins 108. Clips 112 on the latch 107 are sized to engage in the recessed features 113 of the latch receptacle 110 to allow the attachment feature 106 to be secured to the detachable barrel tip 102 for implantation of the assembly 101 and removed after implantation of the assembly.

In embodiments, the mastopexy system comprises an introducer tool with a detachable barrel tip, and an assembly of the elongate member and sheath loaded in the introducer tool. FIG. 6 shows an exploded view of an introducer tool 100 with the assembly 101 of the elongate member and sheath partly loaded in the introducer tool 100. Detail M of FIG. 6 shows an embodiment of the mastopexy system comprising the detachable barrel tip 102 attached to the first end 103 of the tubular section of the introducer tool, the end of the assembly of the elongate member and sheath, and a latch for securing the assembly to the detachable barrel tip. The detachable barrel tip 102 is shown with a rounded tip 104 for blunt dissection. In other embodiments, the detachable barrel tip is fitted with a sharp tip for dissection.

As shown in Detail M of FIG. 6, the mastopexy system may further comprise the assembly 105 of the elongate member and sheath terminating in an attachment feature 106, and a latch 107 with lock pins 108. In embodiments, the attachment feature 106 of the assembly of the elongate member and sheath is connected to the detachable barrel tip 102 by inserting latch 107 through the perforated holes 109 in the attachment feature 106 and into the latch receptacle 110 of the detachable barrel tip 102. In embodiments, the attachment feature 106 is formed by fusion of the end of the elongate member and the end of the sheath, and perforation of the fused section to make holes 109 sized to receive the lock pins 108 on the latch 107. In embodiments, the attachment feature 106 may be secured in the latch receptacle 110 of the detachable barrel tip 102 by insertion of the lock pins 108 through the perforations 109 of the attachment feature 106 and into the recessed holes 111 of the latch receptacle 110. In embodiments, the latch 107 may be secured in the latch receptacle 110 with clips 112 located on the side of the latch that engage in the recessed features 113 of the latch receptacle 110. In embodiments, after implantation, the attachment feature 106 may be removed from the latch receptacle 110 by releasing the clips 112 from the recessed features 113 of the latch receptacle 110.

Figures 7A, 7B, 7C:
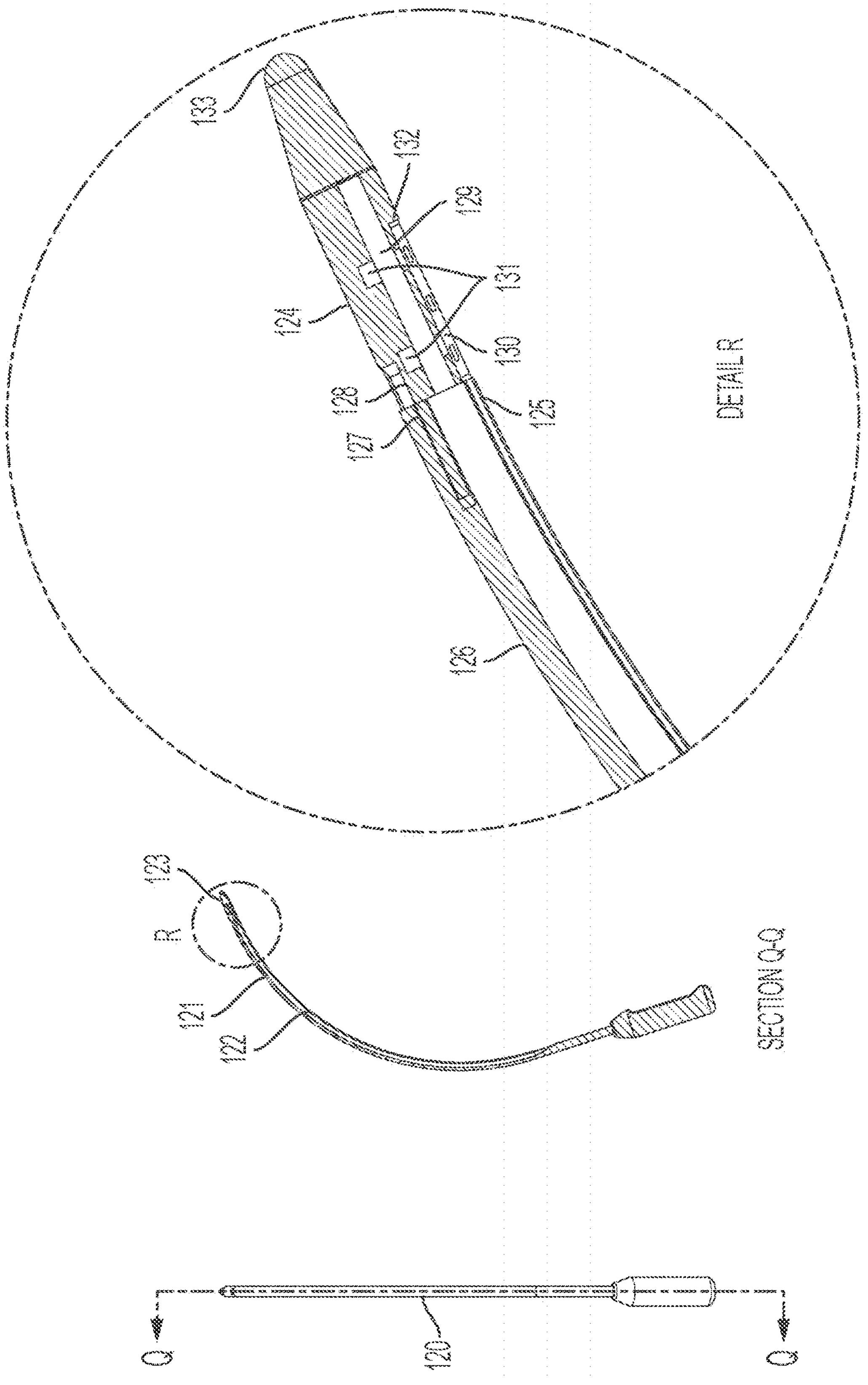
FIG. 7A shows a side view of an introducer tool 120 suitable for use in a mastopexy procedure.
FIG. 7B shows a longitudinal cross-sectional view of the introducer tool shown in FIG. 7A along the axis denoted by Q-Q.

A side view of an introducer tool 120 suitable for use in an embodiment of a mastopexy system is shown in FIG. 7A. FIG. 7B shows a longitudinal cross-sectional view of the introducer tool shown in FIG. 7A along the axis denoted by Q-Q. FIG. 7B shows the tubular section 121, the tubular section's lumen 122, and the detachable barrel tip 123 of the introducer tool. In embodiments, the detachable barrel tip is fastened to the first end of the tubular section of the introducer tool as shown in the enlarged longitudinal cross-sectional view shown in FIG. 7C, corresponding to Detail R shown in FIG. 7B. FIG. 7C shows the detachable barrel tip 124 connected to the first end 125 of the tubular section of the introducer tool 126 by a fastening mechanism. In embodiments, the fastening mechanism allows the detachable barrel tip 124 to be released from the first end 125 of the tubular section of the introducer tool 126. In embodiments, the fastening mechanism of the introducer tool comprises mounting pins 127 on the detachable barrel tip that can be inserted into the first end 125 of the tubular section of the introducer tool 126 (mounting pin 127 shown inserted), and a disengagement notch 128 designed to release the detachable barrel tip 124 from the first end 125 of the tubular section of the introducer tool 126 by releasing the mounting pins 127. In embodiments, the detachable barrel tip 124 comprises a lumen 129 as shown in FIG. 7C for insertion of the attachment feature (not shown) of the assembly of the elongate member and sheath (not shown). In embodiments, the mastopexy system comprises a latch 130 with two lock pins 131 that may be inserted in the latch receptacle 132 with the lock pins 131 located in the detachable barrel tip 124. The detachable barrel tip 124 is shown in FIGS. 7A-C with a sharp cutting tip 133. In embodiments, the detachable barrel tip 133 may be fitted with a blunt dissection tip.

Figure 8B:
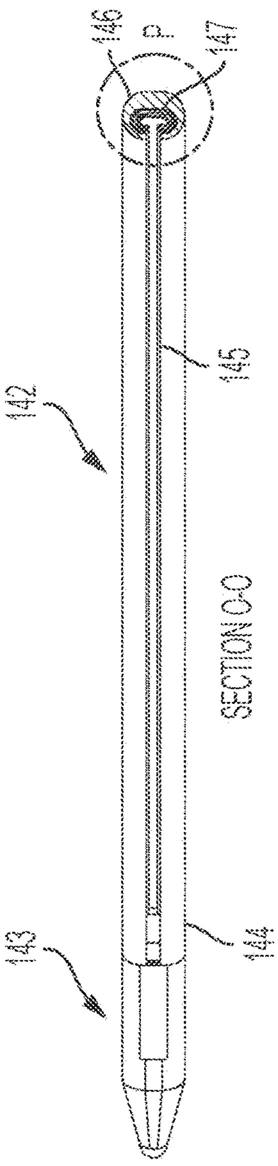
FIG. 8B shows a section of the introducer tool viewed along axis O-O in the direction of the arrows shown in FIG. 8A.
Figure 8C:
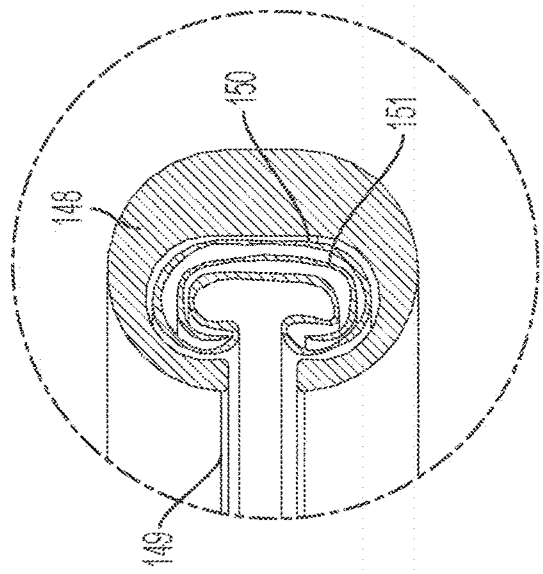
FIG. 8C shows an enlargement of Detail P shown in FIG. 8B. Detail P shown in FIG. 8C shows a cross-sectional view of the tubular section 148 of the introducer tool with a C-shape, a slit 149 in the tubular section of the introducer tool, and a sheath 150 encasing the elongate member 151 formed into a C-shape within the tubular section 148 of the introducer tool. The sheath 150 encasing the elongate member 151 is formed into a C-shape within the tubular section 148.
Figure 8A:
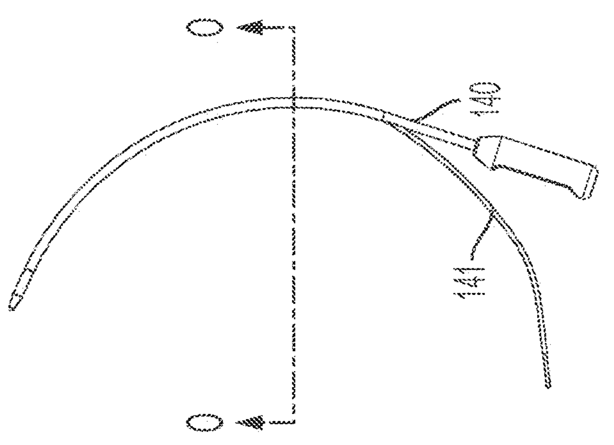
FIG. 8A shows a front view of an introducer tool 140 loaded with an assembly 141 of an elongate member and sheath.

In embodiments, the mastopexy system comprises an introducer tool 140 loaded with an assembly 141 of an elongate member and sheath as is shown in the front view of the system in FIG. 8A. FIG. 8B shows a view of the introducer tool along the axis denoted by O-O in FIG. 8A in the direction of the arrows. FIG. 8B shows the introducer comprising a tubular section 142, a detachable barrel tip 143 connected to the first end 144 of the tubular section 142, a slit 145 in the tubular section 142 of the introducer tool, and a cross-section of the tubular section 146 shown in more detail in Detail P. In embodiments, the assembly 147 of the elongate member and sheath are folded into a C-shape as shown in Detail P. FIG. 8C is an enlargement of Detail P shown in FIG. 8B, and shows in the cross-section view that the tubular section 148 of the introducer tool comprises a C-shaped cross-section, a slit 149 to load and unload the assembly of the elongate member and sheath, and a sheath 150 encasing the elongate member 151 formed into a C-shape within the tubular section 148.

Figure 9:
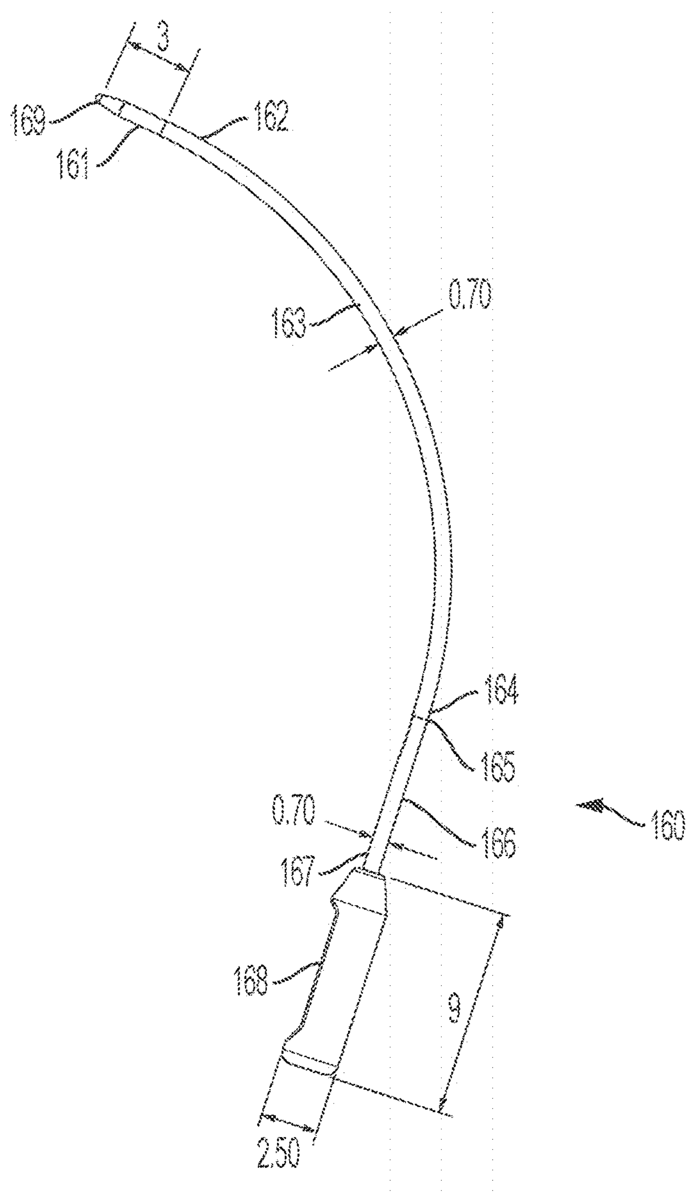
FIG. 9 shows an introducer tool 160 with a detachable barrel tip 161 connected to the first end 162 of a curved tubular section 163 of the introducer tool 160, a second end 164 of the curved tubular section 163 connected to the first end 165 of a straight tubular section 166, and the second end of the straight tubular section 167 connected to a handle 168. The detachable barrel tip 161 is fitted with a cutting tip or blunt dissection tip 169.

An example of the dimensions and design of an introducer tool is shown in FIG. 9. In this embodiment, the introducer tool 160 comprises a detachable barrel tip 161 connected to the first end 162 of a curved tubular section 163, wherein the second end 164 of the curved tubular section 163 is connected to the first end 165 of a straight tubular section 166, and wherein the second end 167 of the straight tubular section 166 is connected to a handle 168. In embodiments, the detachable barrel tip 161, the curved tubular section 163, and the straight tubular section 166 have an outer diameter of 0.7 cm. In embodiments, the detachable barrel tip is fitted with a cutting tip or blunt dissection tip 169, and the total length of the detachable barrel tip and cutting or blunt dissection tip is 3 cm. In embodiments, the handle 168 has an outer diameter of 2.5 cm and a length of 9 cm.

Figure 10:
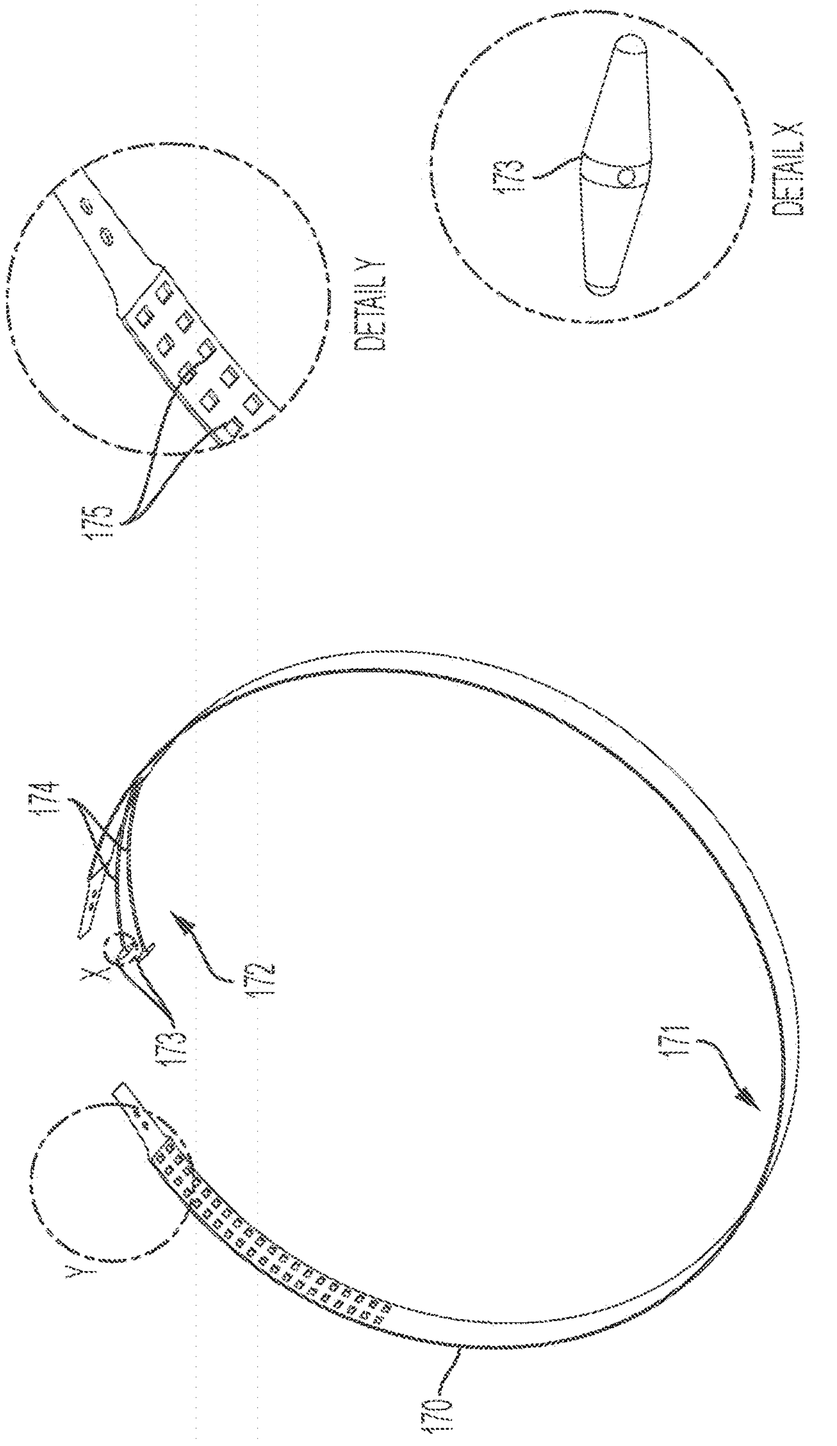
FIG. 10 shows an implant (170) for mastopexy made of an elongate member (171) with a fastening anchor (172) to secure the elongate member in the breast. The fastening anchor (172) is shown with a T-shape formed with a T-cap pin (173) and arms (174) connected to the T-cap pin (173) and elongate member (171).

In embodiments, the mastopexy system comprises an elongate member with one or two fastening anchors to secure the elongate member to tissue. FIG. 10 shows an elongate member 171 with a fastening anchor 172. In embodiments, the fastening anchor has a T-shape. In embodiments, the T-shape fastening anchor is formed by injection molding a T-cap pin, and attaching arms to the ends of the T-cap pin 173. In embodiments, the T-cap pin has a hole sized for passage of a suture to allow the fastening member to be sutured to tissue. In embodiments, the T-cap pin is tapered with the center of the pin having a larger diameter than the ends of the pin. In embodiments, the arms 174 are prepared from monofilament fiber, including, but not limited to, resorbable monofilament fiber. In embodiments, the resorbable monofilament fiber is prepared from P4HB. In embodiments, the monofilament fiber has an average diameter from 0.05 to 0.4 mm and/or from 0.07 to 0.3 mm. In embodiments, the arms of the fastening anchor are attached to the elongate member, for example, by tying, gluing, stapling, or fusing. In embodiments, the arms have a length of 2-10 cm and/or 4-6 cm. In embodiments, the fastening member is attached to the elongate member between 2 and 10 cm from the end of the elongate member.

In embodiments, the mastopexy system may comprise just one introducer tool that is used to implant a first end of the elongate member in the breast, and then is removed from the breast, loaded with the second end of the elongate member, and reinserted in the breast to deliver the second end of the elongate member. However, in some embodiments, the mastopexy system comprises two introducer tools as shown in FIG. 1 so that each end of the elongate member is implanted using a different introducer tool.

In embodiments, the systems for mastopexy are designed for minimally invasive delivery. The implants have a design and properties that allow them to be delivered through a small incision. In embodiments, the implants are designed so that they can be rolled or folded to allow delivery through a small incision. This minimally invasive approach can reduce patient morbidity, scarring and the chance of infection. In embodiments, the implant has shape memory properties that allows it to assume its original shape unaided after it has been delivered to the implant site. For example, the implant may be temporarily deformed by rolling it up into a small diameter cylindrical shape or C-shape for delivery to the implant site, and then allowed to resume its original shape unaided in vivo.

Methods for Implanting the Mastopexy Implants

The implants and systems described herein are most suited for use in breast surgery, and more particularly for mastopexy procedures.

FIGS. 2A-E show a method for performing a breast lift with an exemplary mastopexy implant system. FIG. 2A shows an outline of a patient's breast 10, the breast's NAC 11, and a first introducer tool 12 of an exemplary mastopexy system 13. The method of implantation comprises making a stab incision 14 in the breast (e.g., at the IMF of the lower pole of the breast), and inserting the first introducer tool 12 into the stab incision. The distal end of the introducer tool inserted into the breast may have a detachable barrel tip designed for blunt dissection of breast tissue. In embodiments, the introducer tool is advanced in the breast to form a defined channel, for example, by blunt dissection, by applying a force to the introducer tool in the direction of the arrow 15 shown in FIG. 2A. The first introducer tool is advanced with a circular motion to circumnavigate the patient's breast 20 beneath the skin of the breast as shown in FIG. 2B until the distal end of the first introducer tool 22 of the mastopexy system 23 is positioned in the upper pole of the breast, for example, above the NAC 21. In embodiments, the detachable barrel tip 25 of the introducer tool is then moved in the direction indicated by arrow 26 such that the detachable barrel tip 25 exits the breast. In embodiments, a small incision may be made in the breast to facilitate explanation of the detachable barrel tip 25. In embodiments, the method of implantation comprises detaching the detachable barrel tip 25 from the first introducer tool, and withdrawing the first introducer tool from the breast by moving the tool in the opposite direction to the direction of insertion. The method may include holding the detachable barrel tip or assembly of the sheath covering the elongate member implant attached to the detachable barrel tip while the introducer tool is withdrawn. Holding the detachable barrel tip in this manner prevents the detachable barrel tip from being pulled back into the breast during removal of the first introducer tool.

FIG. 2C shows a patient's breast 30 with NAC 31, the position of the detachable barrel tip 32 after it is explanted from the patient's breast through a small incision 33 in the upper pole of the breast, and the position of the assembly 34 of the elongate member implant covered by the sheath in the breast 30 after removal of the first introducer tool from the breast. Thus, the assembly 34 of the sheath covered elongate member implant is implanted in the breast so that it circumnavigates a first side of the breast beneath the skin of the breast from the site where the introducer tool is introduced to the site where the detachable barrel tip is explanted. After removal of the first introducer tool from the breast, the implanted assembly remains connected to the second introducer tool 35 loaded with the remainder of the assembly of the elongate member implant and sheath for implantation on the opposite side of the breast. In embodiments, the method further comprises inserting into the breast 40 the second introducer tool 42 at the same incision site 43 in the IMF, or lower pole of the breast, which was used to insert the first introducer tool into the breast, as shown in FIG. 2D. After insertion of the second introducer tool 42 into the incision site 43, the second introducer tool 42 is used to form a channel circumnavigating the opposite side of the breast beneath the skin of the breast as shown in FIG. 2D until the detachable barrel tip 44 of the second introducer tool is positioned to be explanted from the upper pole of the breast. The detachable barrel tip 44 may be explanted from the breast 40 at the same site 45 as the detachable barrel tip of the first introducer tool. The detachable barrel tip 44 is explanted by moving the second introducer tool 42 in the direction indicated by arrow 46.

After explanation of the detachable barrel tip 44, the detachable barrel tip 44 or assembly of the sheath covering the elongate member implant attached to the detachable barrel tip is held while the second introducer tool is withdrawn. In embodiments, the method further comprises detaching the detachable barrel tips from the sheath covered elongate member implant, and separating the ends of elongate member implant from the sheaths, for example, by cutting. The sheaths may then be removed from the breast by pulling them in a superior direction, and leaving the elongate member implant circumnavigating the breast with the ends of the elongate member implant slightly exposed from the breast.

FIG. 2E shows the breast 50 of a patient, NAC 51, an implanted elongated member implant 52 circumnavigating the breast beneath the skin of the breast after the sheaths have been removed from the breast, and the ends 53 of the elongate member implant exposed from the breast 50 through the second incision 54. The method further comprises lifting the breast by pulling on the ends 53 of the elongate member implant in a superior direction indicated by arrows 55. Once the breast 50 has been lifted to a satisfactory position, the ends 53 of the elongate member implant are secured beneath the skin. The ends 53 may be secured by tying them together, or by securing the ends 53 to tissue, including, for example, the chest wall. If necessary, the ends of the elongate member implant may be trimmed.

In embodiments, the method of implanting the elongate member implant may comprise just one introducer tool. The one introducer tool is used to implant a first end of the assembly of the sheath covered elongate member implant in the breast. The detachable barrel tip is then detached from the one introducer tool, and the one introducer tool is removed from the breast. The one introducer tool is then loaded with the second end of the assembly of the sheath covered elongate member implant, and implanted on the other side of the breast. The detachable barrel tip is detached from the one introducer tool, and the one introducer tool is removed from the breast.

In embodiments, the method of implanting the implant may comprise the use of an assembly of a single sheath covering the elongate member implant. The assembly may be implanted in the breast as described herein, and the sheath removed from the breast by pulling just one end of the sheath, or by cutting or tearing the sheath to expose the elongate member implant (e.g., at the first incision site), and pulling the cut pieces of sheath to remove them from the breast.

In embodiments, the method of implanting the implant comprises forming a channel for the implant in the breast by dissection, for example, by blunt dissection.

In embodiments, the method of implanting the implant comprises introducing the assembly comprising the sheath covered elongate member implant in the upper pole of the breast.

In embodiments, the method of implanting the implant comprises implanting the assembly comprising the sheath covered elongate member implant using just one incision in the breast. In this embodiment, a single incision is made, for example, at the IMF or in the lower pole of the breast, an introducer tool loaded with the assembly comprising the elongate member implant and sheath is introduced at the incision site, and the introducer tool is used to completely circumnavigate the breast beneath the skin of the breast in order to implant the assembly comprising the sheath covered elongate member implant. The detachable barrel tip of the introducer tool is then explanted at the incision site, detached from the introducer tool, and the introducer tool is removed from the breast. After removing the sheath or sheaths from the breast, tension is applied to the ends of the elongate member implant in order to lift the breast, and the ends of the elongate member implant are secured and trimmed if necessary.

In embodiments, the method of lifting the breast comprises: providing an implant comprising a unitary elongate member implant, with a first end and a second end, sized to circumnavigate the breast, providing one or more introducer tools, using the one or more introducer tools to insert the implant in a breast so that the implant circumnavigates the upper and lower poles of the breast beneath the skin of the breast, removing the one or more introducer from the breast, and using the implant to lift or cinch the breast.

In embodiments, the method of lifting the breast further comprises providing an implant comprising an elongate member, wherein the elongate member is a tape, film, porous film, textile, fabric, knitted mesh, woven mesh, non-woven mesh, or de-tanged mesh.

In embodiments, the method of lifting the breast comprises: providing one or more introducer tools and an assembly comprising an implantable unitary elongate member implant, with a first end and a second end, sized to circumnavigate the upper and lower poles of the breast, and one or more sheaths connected to the elongate member near one or both ends of the elongate member and at least partially enclosing the elongate member, using the one or more introducer tools to insert the assembly in the breast so that the elongate member circumnavigates the upper and lower poles of the breast beneath the skin of the breast, removing the one or more introducer tools from the breast, removing the one or more sheaths from the breast and using the elongate member implant to lift or cinch the breast. In embodiments, the method further comprises: providing the elongate member implant with an attachment feature, and using an introducer tool to insert the elongate member implant in the breast by connecting the attachment feature to the introducer tool. In embodiments, the method further comprises: providing the elongate member implant with an attachment feature at both ends of the elongate member, and using one or more introducer tools to insert the elongate member in the breast by connecting the attachment features to one or more introducer tools.

In embodiments, the method further comprises: providing an introducer tool with a tubular section with a first end and a second end, wherein the tubular section comprises a slit running at least part of its length with an inlet opening, and wherein the first end of the tubular section is connected to a detachable barrel tip and the second end of the tubular section is connected to a handle, inserting, at least partly, an assembly of the elongate member implant and sheath through the inlet opening into the tubular section of the introducer tool prior to implanting the elongate member implant in the breast. In embodiments, the method further comprises: providing the elongate member with an attachment feature, and an introducer tool with a tubular section with a first end and a second end, wherein the tubular section comprises a slit running at least part of its length with an inlet opening, and wherein the first end of the tubular section is connected to a detachable barrel tip and the second end of the tubular section is connected to a handle, and wherein the detachable barrel tip is provided with a latch receptacle for securing the attachment feature of the elongate member to the detachable barrel tip and a terminal blunt dissection tip or cutting tip, and using the terminal blunt dissection tip or cutting tip to form a channel that circumnavigates the upper and lower poles of the breast for implantation of the elongate member. In embodiments, the method further comprises: providing an introducer tool with a detachable barrel tip, wherein the detachable barrel tip comprises a fastening mechanism for attachment and detachment of the detachable barrel tip from the introducer tool, attaching the assembly to the detachable barrel tip, inserting the introducer tool in the breast, and using the fastening mechanism to detach the barrel tip from the introducer tool after insertion of the assembly in the breast. In embodiments, the method further comprises: providing an introducer tool with a detachable barrel tip fitted with a latch receptacle, a latch, and an elongate member with an attachment feature, and inserting the latch through the attachment feature and into the latch receptacle to secure the elongate member to the detachable barrel tip. In embodiments, the method further comprises: providing an introducer tool with a detachable barrel tip fitted with a latch receptacle, a latch with one or more lock pins, and an elongate member with an attachment feature, and inserting the lock pins of the latch through the attachment feature and into the latch receptacle to secure the elongate member to the detachable barrel tip.

In embodiments, the method further comprises providing the elongate member in the form of a tape, film, porous film, textile, knitted mesh, woven mesh or de-tanged mesh. In embodiments, the method further comprises: providing the elongate member with one or two attachment anchors, and securing the one or two attachment anchors in the breast after the breast has been lifted, for example, by suturing the one or two attachment anchors to tissue. In embodiments, the method further comprises providing the elongate member made from one or more polymers, wherein the polymers are synthesized from, or comprise, one or more of the following monomers: glycolic acid, lactic acid, 1,4-dioxanone, trimethylene carbonate, 3-hydroxybutyric acid, 4-hydroxybutyric acid, ε-caprolactone, 1,4-butanediol, adipic acid, and succinic acid. In embodiments, the method further comprises affixing the elongate member implant to tissue after lifting or cinching the breast, or tying the ends of the elongate member together after lifting or cinching the breast.

Modifications and variations of the methods and compositions will be apparent from the foregoing detailed description and are intended to come within the scope of the appended claims.

The present invention will be further understood by reference to the following non-limiting examples.

EXAMPLES

Example 1: Preparation of a Minimally Invasive Mastopexy System

A minimally invasive mastopexy system may be prepared from (i) an elongate member made by knitting a construct of poly-4-hydroxybutyrate (P4HB), (ii) two sheaths made of low density polyethylene (LDPE), and (iii) two stainless steel curved introducer tools.

The knitted P4HB elongate member may be prepared by warp knitting size 6-0 P4HB monofilament (P4HB Mw 340 kDa), heat setting the knit at 54° C. for 5 minutes, and laser cutting the knit to form an elongate member implant with a first end and second end, and with dimensions of 10 mm wide by 55 cm long. The elongate member has an average tensile strength of 78 N, an average pore size of 0.36 $mm^2$, and a thickness of 0.65 mm.

Two sheaths of LDPE are prepared, each with a first end and a second end. Each sheath has a diameter of 8 mm (or 14 mm when the sheath was flattened), a length of 20 cm, and a wall thickness of 0.07 mm. The first end of the elongate member implant is placed inside the second end of the first sheath, and the elongate member slid inside the first sheath until its first end is aligned with the first end of the first sheath. The second end of the elongate member implant is placed inside the second end of the second sheath, and the elongate member slid inside the second sheath until its second end is aligned with the first end of the second sheath. In this manner an assembly of the elongate member and sheaths may be formed with 20 cm sections of the elongate member measured from its first and second ends enclosed in the sheaths, and 15 cm of the middle of the elongate member not enclosed in a sheath. To secure the sheaths in place, each sheath is thermally fused to the elongate member at the first and second ends of the elongate member. After fusion of the sheaths to the elongate member, two 2 mm diameter holes are cut through each fused section spaced 8 mm apart to form attachment features at each end of the fused sections of the assembly of the elongate member and sheath.

Two blunt tipped curved introducer tools are prepared using 316L stainless steel to machine the tubular sections, and medical grade polypropylene to prepare the handles. The tubular sections of the tools measure 38 cm in length, and consist of three sections: a first section with a straight detachable barrel tip measuring 2.5 cm in length, a second section with a first end, a second end, and a main body with a cold bent 20 cm curvature radius, and a third section with a first end, a second end, and a long straight section measuring 7 cm with an inlet opening at the first end. The tubular sections of the introducer tools are formed so that the detachable barrel tips can be attached or removed from the first ends of the second sections of the tubular sections. For delivery of the sheathed elongate member assembly, the main bodies of the needles are machined so that they have C-shaped cross-sections of 10 mm by 14 mm with inner cavities (for the elongate member) having C-shaped cross-sections of 7 mm by 9 mm. The third sections of the tubular sections are machined with an inlet opening at the first ends measuring 0.5 cm by 1.0 cm. The second sections of the tubular sections are connected to the first end of the third sections so that channels in the tubular sections are formed between the inner cavities of the second sections and the inlet openings of the third sections. The handles are connected to the second ends of the third sections of the tubular sections. The detachable barrel tips are machined with (a) blunt tips for blunt dissection of breast tissue, (b) latch receptacles to receive a fused end of the assembly of the elongate member and sheath, (c) mounting pins for insertion in the first ends of the second sections of the tubular sections, and (d) disengagement notches to release the detachable barrel tips from the first ends of the second sections of the tubular sections. The latch receptacles are also machined with recessed features to receive securing knobs located on the latches. The latches are machined from 316L stainless steel, with dimensions of 4 mm by 15 mm, to fit in the latch receptacles of the detachable barrel tips with pins for insertion through the fused assembly of the elongate member and sheath, and knobs on the latches designed to engage in the latch receptacles to secure the latches in place.

The mastopexy system is assembled by rolling the assembly of the elongate member and the two sheaths. A first fused end of the rolled assembly is then inserted in a first introducer tool by passing it through the inlet opening in the third section of the tubular section and into the inner cavity of the second section of the tubular section until the first fused end exited the first end of the second section of the tubular section and could be placed in the latch receptacle of the detachable barrel tip with at least part of the assembly of the elongate member and first sheath retained inside the cavity of the second section of the tubular section of the first introducer tool. The first fused section of the assembly is secured to the detachable barrel tip by insertion of a latch with two pins through the two 2 mm diameter holes in the first fused section, and into the latch receptacle of the detachable barrel tip with the knobs on the latch engaging in the recessed features of the latch receptacle. The second fused end of the rolled assembly is then inserted in the second introducer tool in the same manner described for insertion of the first fused end so that the second fused end could be placed and secured with a second latch in the detachable barrel tip of the second introducer tool, and at least part of the assembly of the second sheath and elongate member retained inside the cavity of the second section of the tubular section of the second introducer tool.

Example 2: Preparation of a Minimally Invasive Breast Suspension System with Fastening Anchors In this example, a mastopexy system may be prepared that is fitted with two fastening anchors to allow the elongate member to be secured in place after lifting the breast. FIG. 10 shows an implant (170) containing an elongate member (171) with fastening anchors (172) at one end. The fastening anchors are incorporated into the elongate member in the regions adjacent to locations where the elongate member and sheaths are fused together. The fastening anchors have a T-shape, and are formed with a T-cap pin (173) that is injection molded, and arms (174) that are connected to the T-cap pin and elongate member. The T-cap pin features a center hole sized to thread suture through for fixation of the fastening anchor to tissue in the breast. The dimensions of the T-cap pin are 1 cm in length with a diameter of 2 mm at the center of the pin tapering to 1 mm at each end of the pin. The T-cap pin is made from P4HB (Mw 340 kDa). The arms of the fastening anchor are formed from size 3-0 P4HB monofilament, and each has a length of 5 cm. The elongate member (171) has a total length of 30 cm. The arms (174) of each fastening anchor (172) are attached to the elongate member at a distance of 5 cm from each end of the elongate member by tying the size 3-0 P4HB monofilament arms of each fastening anchor to the elongate member.

In order to provide a means to fixate the T-cap pin (173) near the other end of the elongate member (shown in FIG. 10 as Detail Y), the other end of the elongate member (175) may be formed with pores. The pores are formed with sufficient dimensions to allow insertion of the pin of the T-cap pin in the elongate member. For example, the pores may be formed with dimensions of 1.5×3 mm and arranged in an array. A suitable array may have 2×20 pores. When the elongate member is formed from a P4HB textile, for example a dense warp knit crochet design made from suture size 6-0 P4HB monofilament, the array of pores may be formed using a rectangular array of 2×20 needles, each with dimensions of 1.5×3 mm, that is heated to 57° C., and pushed through the elongate member in the region shown as Detail Y. Once inserted, the perforated elongate member may be heat set, for example, at 54° C. for 5 minutes, and then cooled. Removal of the array of needles from the elongate member, leaves a structure shown in Detail Y with an array of heat set pores.

We claim:

1. A mastopexy system comprising:

an implantable unitary elongate member, with a first and a second end, sized to circumnavigate a breast beneath the skin, and a sheath connected to the elongate member and at least partially enclosing the member; and an introducer tool configured to introduce the elongate member and the sheath beneath the skin to circumnavigate the breast, the introducer tool including a tubular section, a barrel tip detachably connected to a first end of the tubular section and a handle connected to a second end of the tubular section, the tubular section having a length from the first end to the second end and a slit running along at least part of the length, wherein the slit is configured to receive at least part of the elongate member and the sheath.

2. The mastopexy system of claim 1, wherein the sheath is fused to the elongate member.

3. The mastopexy system of claim 1, wherein the elongate member comprises an attachment feature to connect the elongate member to the introducer tool.

4. The mastopexy system of claim 3, comprising attachment features at or adjacent to the first and second ends of the elongate member, and each attachment feature is connected to the introducer tool.

5. The mastopexy system of claim 1, wherein the tubular section of the introducer tool further comprises an inlet opening, and an assembly of the member and sheath is at least partly inserted in the tubular section of the introducer tool through the inlet opening in the tubular section.

6. The mastopexy system of claim 1, wherein the unitary elongate member is a tape, film, porous film, textile, braid, knitted, woven, or nonwoven mesh or fabric, or de-tanged mesh.

7. The mastopexy system of claim 1, wherein the unitary elongate member comprises one or more polymers, and wherein the polymers are synthesized from, or comprise, one or more of the following monomers: glycolic acid, lactic acid, 1,4-dioxanone, trimethylene carbonate, 3-hydroxybutyric acid, 4-hydroxybutyric acid, ε-caprolactone, 1,4-butanediol, adipic acid, and succinic acid.

8. The mastopexy system of claim 1, wherein the unitary elongate member further comprises one or more fastening anchors, wherein the fastening anchors are used to secure the elongate member to tissue.

9. The mastopexy system of claim 1, wherein the unitary elongate member comprises at least one property selected from the group consisting of (i) a suture pullout strength of at least 1 kgf, (ii) a burst strength of 0.1 to 100 kg, (iii) a thickness of at least 0.05 mm, (iv) an areal density of 5 to 800 g/m2, and (v) a pore diameter of 5 μm to 10 mm.

10. A method of lifting or cinching a breast, comprising:

providing one or more introducer tools and the breast implant of claim 1, using the one or more introducer tools to insert the breast implant in a breast so that the breast implant circumnavigates upper and lower poles of the breast beneath the skin, removing the one or more introducer tools from the breast, and using the breast implant to lift or cinch the breast.

11. The mastopexy system of claim 1, wherein the slit is configured to receive at least part of the elongate member and the sheath.

12. The mastopexy system of claim 1, wherein the slit runs along a majority of the length of the tubular section.

13. The mastopexy system of claim 4, wherein the detachable barrel tip comprises a latch receptacle for securing the attachment feature of the member to the detachable barrel tip, and a terminal blunt dissection tip or cutting tip.

14. The mastopexy system of claim 13, further comprising a latch, wherein the attachment feature of the member can be secured to the detachable barrel tip of the introducer tool by inserting the latch through the attachment feature of the member and into the latch receptacle.

15. The mastopexy system of claim 14, wherein the latch comprises one or more lock pins.

16. The mastopexy system of claim 1, wherein the introducer tool comprises a fastening mechanism for attachment and detachment of the detachable barrel tip from the first end of the tubular section.

17. The mastopexy system of claim 16, wherein the fastening mechanism comprises one or more mounting pins that attach the detachable barrel tip to the first end of the tubular section of the introducer tool, and a disengagement notch for releasing the detachable barrel tip from the first end of the tubular section of the introducer tool.

18. A method of lifting or cinching a breast, comprising:

providing one or more introducer tools, wherein at least one introducer tool of the one or more introducer tools includes a tubular section, a barrel tip detachably connected to a first end of the tubular section and a handle connected to a second end of the tubular section, the tubular section having a length from the first end to the second end and a slit running along at least part of the length;

providing a breast implant comprising:

an assembly of an implantable unitary elongate member, with a first and a second end, sized to circumnavigate upper and lower poles of the breast beneath the skin, and one or more sheaths connected to the member near one or more ends of the unitary elongate member and at least partially enclosing the unitary elongate member, wherein the slit is configured to receive at least part of the unitary elongate member and the one or more sheathes;

using the one or more tools to insert the assembly in the breast so that the member circumnavigates the upper and lower poles of the breast beneath the skin;

removing the one or more introducer tools from the breast;

removing the one or more sheaths from the breast; and using the unitary elongate member to lift or cinch the breast.

19. The method of claim 18, further comprising: providing the unitary elongate member with an attachment feature, and using an introducer tool to insert the member in the breast by connecting the attachment feature to the introducer tool.

20. The method of claim 18, wherein the slit is configured to receive at least part of the unitary elongate member and the one or more sheaths.

21. The method of claim 18, wherein the slit runs along a majority of the length of the tubular section.

* * * * *